US007569547B2

(12) United States Patent
Lindberg et al.

(10) Patent No.: US 7,569,547 B2
(45) Date of Patent: Aug. 4, 2009

(54) INHIBITING FURIN WITH POLYBASIC PEPTIDES

(75) Inventors: Iris Lindberg, Baltimore, MD (US); Angus Cameron, Bristol (GB); Richard A. Houghten, Vero Beach, FL (US); Jon Richard Appel, Cardiff, CA (US)

(73) Assignees: Board of Supervisors of Louisiana State University and Agricultural and Mechanical College, Baton Rouge, LA (US); Torrey Pines Institute for Molecular Studies, San Diego, CA (US)

( * ) Notice: Subject to any disclaimer, the term of this patent is extended or adjusted under 35 U.S.C. 154(b) by 173 days.

(21) Appl. No.: 11/408,519

(22) Filed: Apr. 21, 2006

(65) Prior Publication Data

US 2006/0241050 A1  Oct. 26, 2006

Related U.S. Application Data

(62) Division of application No. 09/906,311, filed on Jul. 16, 2001, now Pat. No. 7,033,991.

(51) Int. Cl.
*A61K 38/00* (2006.01)
*C07K 16/00* (2006.01)

(52) U.S. Cl. .............................. 514/13; 514/14; 514/15; 514/16; 514/17; 514/18; 530/326; 530/327; 530/328; 530/329; 530/330

(58) Field of Classification Search ....................... None
See application file for complete search history.

(56) References Cited

FOREIGN PATENT DOCUMENTS

| WO | WO92/07871 | | 5/1992 |
| WO | WO 97/18826 | | 5/1997 |
| WO | WO 01/66127 | * | 9/2001 |
| WO | WO 01/83554 A1 | | 11/2001 |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320.*
Gura (Science, 1997, 278:1041-1042).*
Jain (Sci. Am., 1994, 271:58-65).*
Johnson et al, Cancer Treatment Reviews, vol. 2 p. 1 (1975).*
Bae et al JBC vol. 275 p. 13588 (May 2000).*
Angliker, H., "Synthesis of tight binding inhibitors and their action on the proprotein-processing enzyme furin," *J. Med. Chem.*, vol. 38, pp. 4014-4018 (1995).
Basak, A. et al., *Int. J. Pept. Protein Res.*, vol. 44, pp. 253-261 (1994) (Abstract).
Basak, a. et al., "Inhibition of proprotein convertases-1, -7 and furin by diterpines of Andrographis paniculata and their succinoyl esters," *Biochem. J.* 338, pp. 107-113 (1999).
Cameron, A. et al., "Polyarginines are potent furin inhibitors," *J. Biol. Chem...* vol. 275, pp. 36741-36749 (2000).
Coyle, A. et al., "Role of Cationic Proteins in the Airway," *Am. J. Respir. Crit. Care Med.*, vol. 150, pp. S63-S71 (1994).
Frigas, E. et al., "Elevated Levels of the eosinophil Granule Major Basic Protein in the Sputum of Patients with Bronchial Asthma," *Mayo Clin. Proc.*, vol. 56, pp. 345-353 (1981).
Gordon et al., "Proteolytic Activation of Bacterial Toxins: Role of Bacterial and Host Cell Proteases," Infect. Immun. vol. 62, pp. 333-340 (1994).
Gudmundsson, S. et al., "Murine thigh infection model," in O. Zak et al. (Eds.), *Handbook of Animal Models of Infection: Experimental Models in Antimicrobial Chemotherapy*, pp. 137-144 (1999).
Hallenberger, S. et al., "Inhibition of furin-mediated cleavage activation of HIV-1 glycoprotein GP160," *Nature*, vol. 360, pp. 358-361 (1992).
Jean, J. et al., "$\alpha_1$-Antitrypsin Portland, a bioengineered serpin highly selective for furin: Application as an antipathogenic agent," *Proc. Natl. Acad. Sci. USA*, vol. 95, pp. 7293-7298 (1998).
Johansen, H. et al., "Rat model of chronic *Pseudomonas aeruginosa* lung infection," in O. Zak et al. (Eds.), *Handbook of Animal Models of Infection: Experimental Models in Antimicrobial Chemotherapy*, pp. 517-526 (1999).
Ko, K. et al., *Am. J. Physiol.*, vol. 277, pp. L811-L815 (1999).
Komiyama, T. et al., "Engineered eglin c variants inhibit yeast and human proprotein processing proteases, Kex2 and furin," *Biochem.*, vol. 39, pp. 15156-15165 (2000).
Krysan, D. et al., *J. Biol. Chem.*, vol. 274, pp. 23229-23234 (1999).
Lu, W. et al., "$Arg^{15}$-$Lys^{17}$-$Arg^{18}$ turkey ovomucoid third domain inhibits human furin," *J. Biol. Chem.*, vol. 268, pp. 14583-14585 (1993).
Mitchell, D. et al., "Polyarginine enters cells more efficiently than other polycationic homopolymers," *J. Peptide Res.*, vol. 56, pp. 318-325 (2000).
Molloy, S. et al., "Bi-cycling the furin pathway: from TGN localization to pathogen activation and embryogenesis," *Trends in Cell Biology*, vol. 9, pp. 28-35 (1999).

(Continued)

*Primary Examiner*—Sheela J Huff
(74) *Attorney, Agent, or Firm*—John H. Runnels; Bonnie J. Davis

(57) ABSTRACT

Small, polybasic peptides are disclosed that are effective as furin inhibitors, e.g. hexa- to nona-peptides having L-Arg or L-Lys in most positions. Removing the peptide terminating groups can improve inhibition of furin. High inhibition was seen in a series of non-amidated and non-acetylated polyarginines. The most potent inhibitor identified to date, nona-L-arginine, had a $K_i$ against furin of 40 nM. Non-acetylated, poly-D-arginine-derived molecules are preferred furin inhibitors for therapeutic uses, such as inhibiting certain bacterial infections, viral infections, and cancers. Due to their relatively small size, these peptides should be non-immunogenic. These peptides are efficiently transported across cell membranes.

9 Claims, 12 Drawing Sheets

OTHER PUBLICATIONS

Peinado, Juan R. et al., "Cross-Inhibition Between Furin and Lethal Factor Inhibitors," Biochemical and Biophysical Research Communications, vol. 321, pp. 601-605 (2004).

Sarac, Miroslav et al., "Protection Against Anthrax Toxemia by Hexa-D-Arginine in Vitro and in Vivo," Infection and Immunity, vol. 72, pp. 602-605 (2004).

Sarac, Miroslav et al., "The Furin Inhibitor Hexa-D-Arginine Blocks the Activation of *Pseudomonas aeruginosa* Exotoxin A.In Vivo," Infection and Immunity, vol. 70, No. 12, pp. 7136-7139 (2002).

Shinde, U. et al., *Semin. Cell Dev. Biol.*, vol. 11, pp. 35-44 (2000);.

Vepa, S. et al., *Am. J. Physiol.*, "Activation of endothelial cell phospholipase D by polycations," vol. 272, pp. L608-L613 (1997).

Zhong, M. et al., *J. Biol. Chem.*, vol. 274, pp. 33913-33920 (1999).

\* cited by examiner

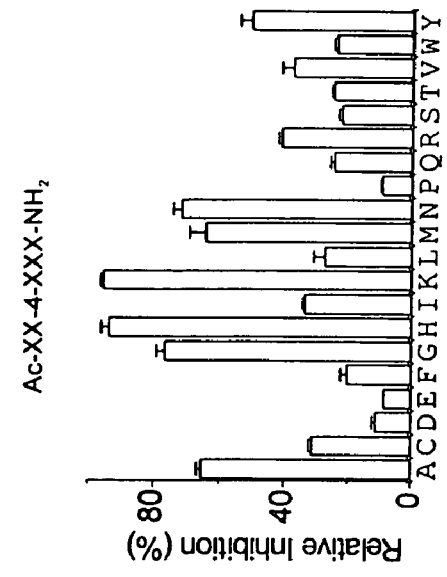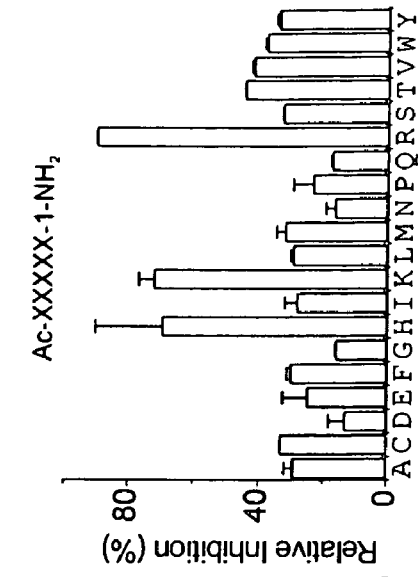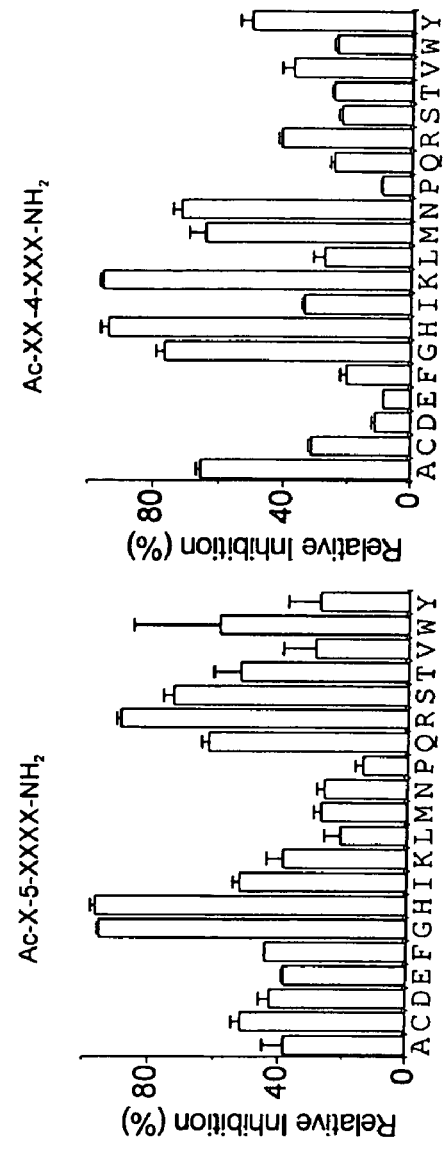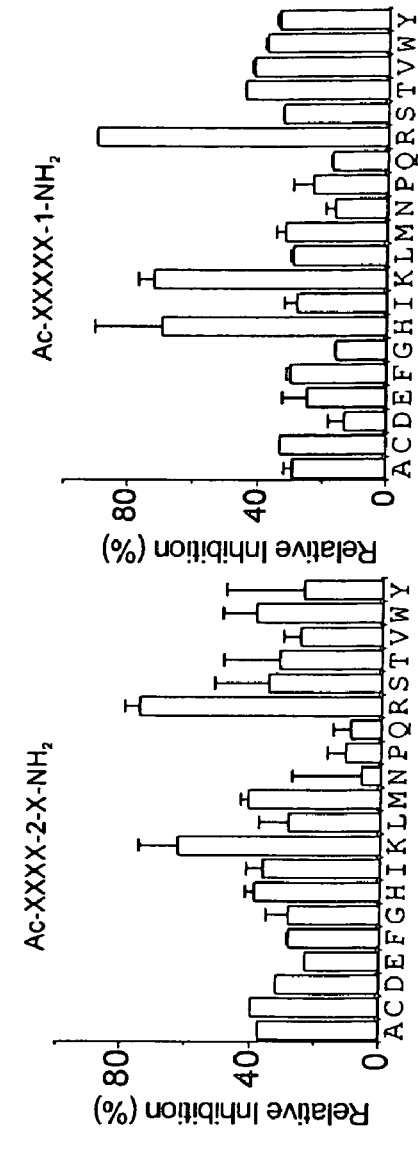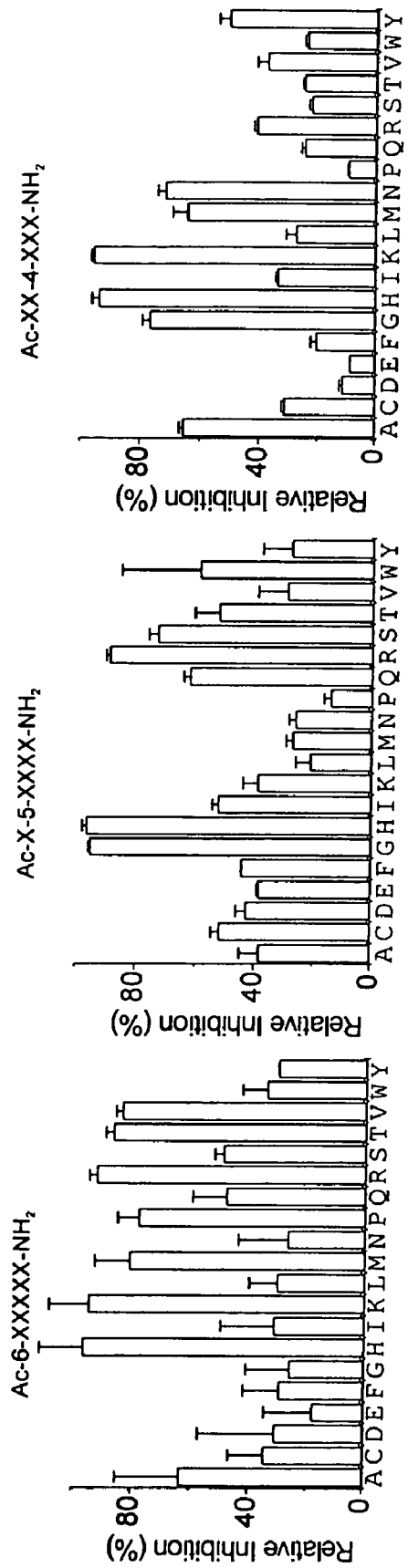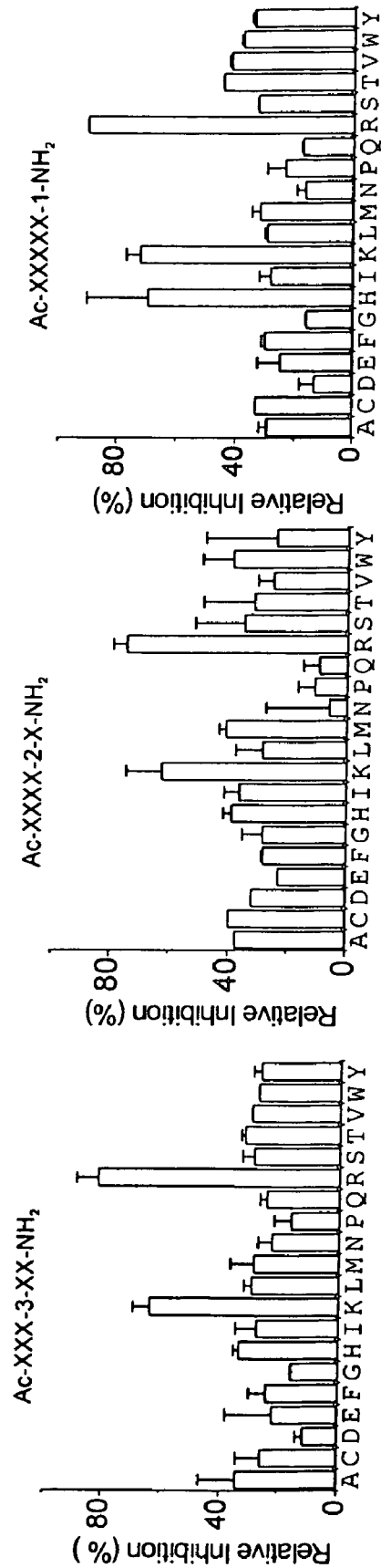

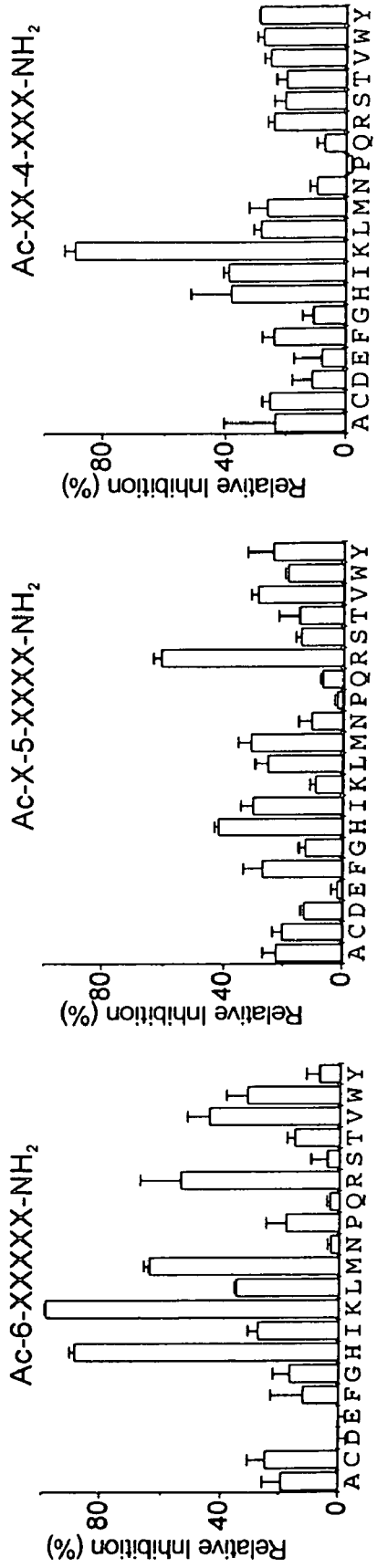
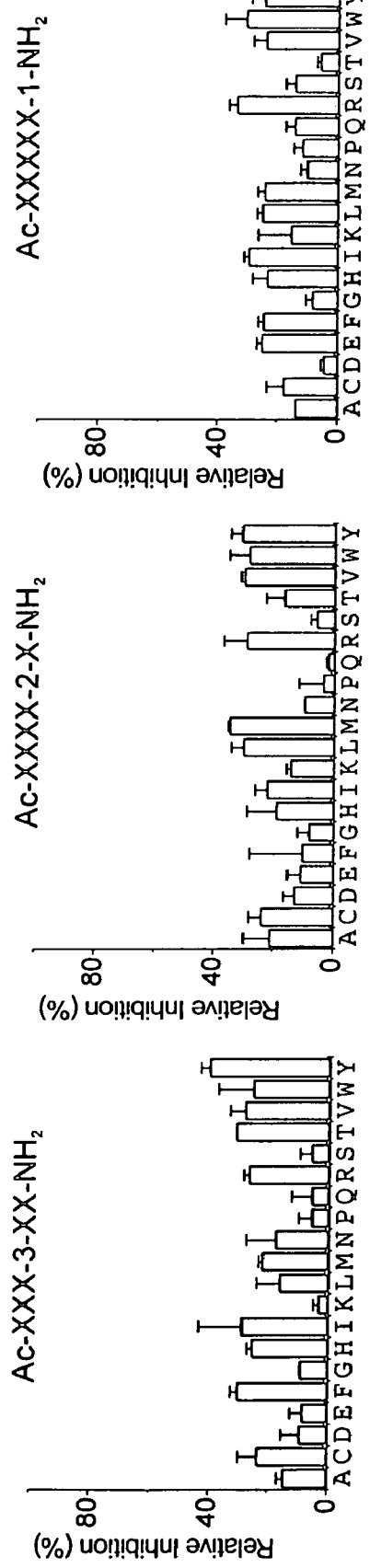
Fig. 4(g), Fig. 4(h), Fig. 4(i), Fig. 4(j), Fig. 4(k), Fig. 4(l)

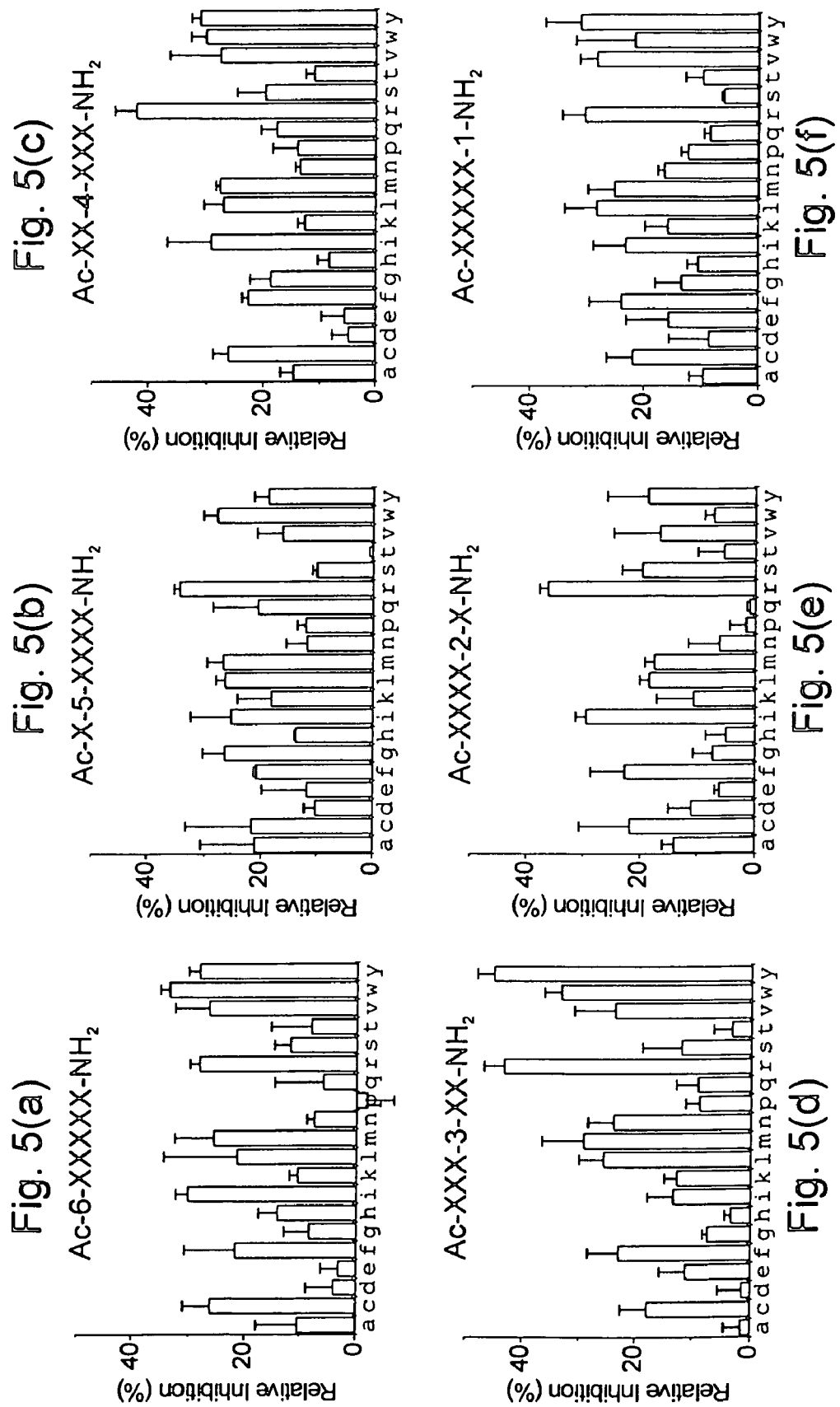

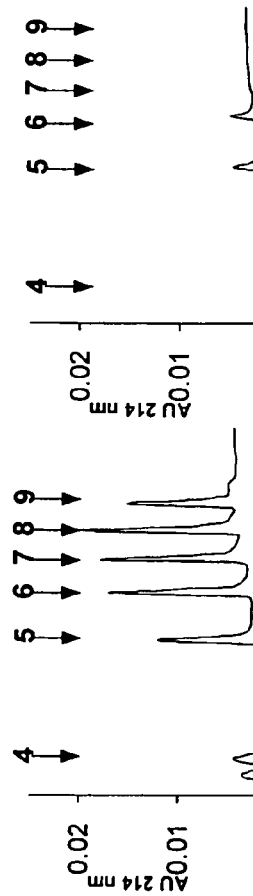
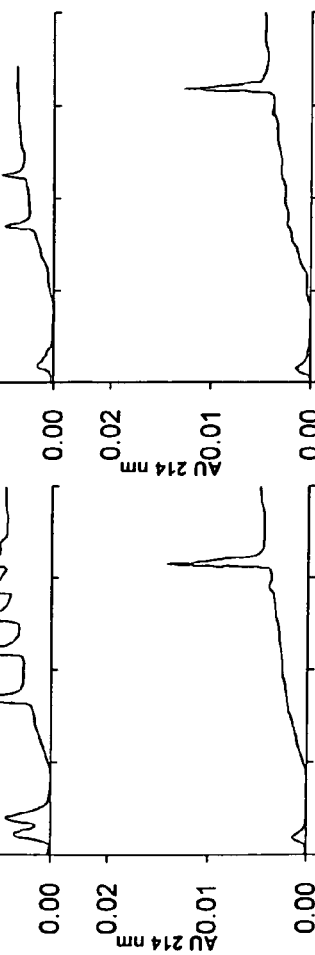
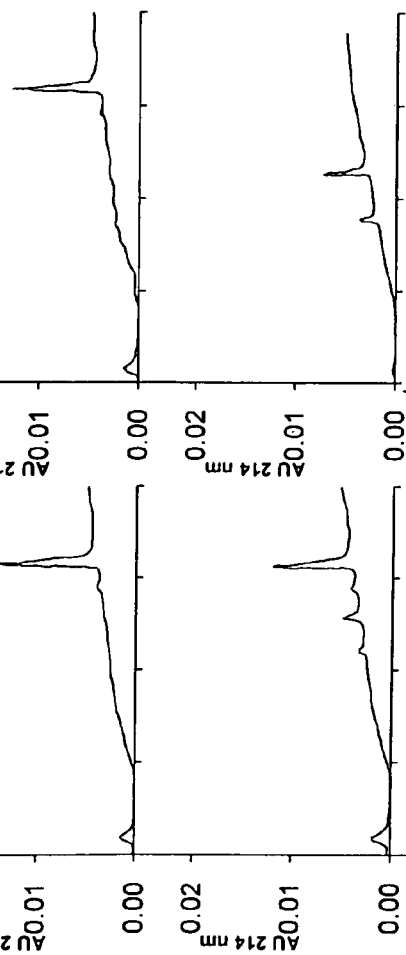
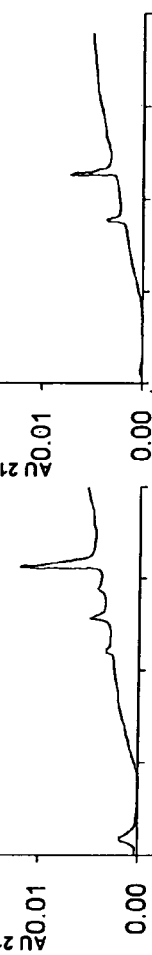
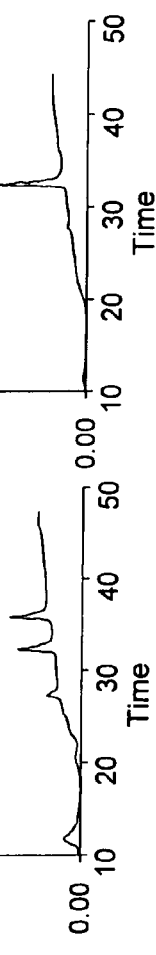

INHIBITING FURIN WITH POLYBASIC PEPTIDES

This application is a divisional of co-pending application Ser. No. 09/906,311, filed Jul. 16, 2001, now allowed with the issue fee paid; the entire disclosure of which is incorporated by reference.

The development of this invention was funded in part by the Government under grant number DA05084 awarded by the National Institutes of Health. The Government has certain rights in this invention.

This invention pertains to the inhibition of furin, which can be used in inhibiting certain bacterial infections, viral infections, and cancers.

Furin, a ubiquitous serine endoprotease, has been implicated in the activation of certain bacterial toxins and viral glycoproteins, as well as in the metastatic progression of certain tumors. Inhibitors of furin can be useful in inhibiting bacterial infections, viral infections, and tumors that depend on furin. While some inhibitors of furin have previously been reported, they have had high molecular weights, making them relatively expensive and potentially immunogenic; or they are toxic. To the inventors' knowledge, there have been no small, non-toxic nanomolar inhibitors of furin reported previously.

Furin is a calcium-dependent, membrane-bound serine endoproteinase. It is a member of the "subtilisin-like" proprotein/prohormone convertase (PC) family of enzymes. The PC family of hormones includes those known as furin; PACE4; PC2; PC1 (or PC3); PC4; PC5 (or PC6A); PC6B; and LPC (or PC7 or PC8). Furin has a ubiquitous tissue distribution. It cycles between the trans-Golgi network ("TGN"), the cell surface, and the endosomes, directed by defined sequences within furin's cytosolic tail. Furin processes not only intracellular growth factors and serum proteins, but also extracellular matrix proteins and cell surface receptors. Furin has been reported to cleave proproteins at the consensus sequence -Arg-Xaa-Lys/Arg-Arg-↓ (SEQ ID NO 1). The minimum consensus sequence has been reported to be -Arg-Xaa-Xaa-Arg-↓ (SEQ ID NO 2). See H. Angliker, "Synthesis of tight binding inhibitors and their action on the proprotein-processing enzyme furin," *J. Med. Chem.*, vol. 38, pp. 4014-4018 (1995).

In addition to these benign physiological roles, furin also plays a role in many pathological pathways, including the cleavage and activation of bacterial toxins and viral coat proteins, such as toxins and other proteins from HIV-1 gp160, Newcastle-disease virus$_o$, measles virus$_o$, human cytomegalovirus glycoprotein B, anthrax toxin, *Pseudomonas* endotoxin A, diphtheria toxin, and Shiga toxin. Furin has also been implicated in assisting the maturation of the matrix-metalloproteinases MT1-MMP and stromelysin-3, a process associated with metastatic progression in various tumors. Thus non-toxic compounds that inhibit furin could be useful as a therapeutic agent against various bacteria, viruses, and tumors.

S. Molloy et al., "Bi-cycling the furin pathway: from TGN localization to pathogen activation and embryogenesis," *Trends in Cell Biology*, vol. 9, pp. 28-35 (1999), is a review of the role of furin in numerous biological pathways, including pathogenesis induced by several bacteria and viruses.

There have been reports that the P6, P1' and P2' positions contribute to furin catalysis. Like furin substrates, furin inhibitors also require that certain subsites be occupied by basic amino acid residues. For example, the third domain of turkey ovomucoid has been engineered (KPACTLE$^{19}$→KPRCKRE$^{19}$) (SEQ ID NOs 3 and 4, respectively) to attempt to increase its specificity towards furin; however the reported equilibrium constant of $1.1 \times 10^7$ M$^{-1}$ indicated that it was only a moderate inhibitor. See W. Lu et al., "Arg$^{15}$-Lys$^{17}$-Arg$^{18}$ turkey ovomucoid third domain inhibits human furin," *J. Biol. Chem.*, vol. 268, pp. 14583-14585 (1993). Inhibition of furin in the sub-nanomolar range has been accomplished by bioengineering the reactive site loop of an α1-antitrypsin variant, α1-antitrypsin Portland or α1-PDX, to contain a minimal furin consensus sequence (LEAIMPS$^{359}$→LERIMRS$^{359}$) (SEQ ID NOs 5 and 6, respectively). Kinetic analysis showed that a portion of bound α1-PDX operates as a tight-binding suicide inhibitor, forming an SDS-stable complex with furin; an alternative pathway involves cleavage and release of α1-PDX. The bait region of the general protease inhibitor α2-macroglobulin (α2M) has been mutated (RVGFYESDVM$^{690}$→RVRSKRSLVM$^{690}$) (SEQ ID NOs 7 and 8, respectively) to attempt to produce a specific furin inhibitor.

The ovalbumin-type serpin human proteinase inhibitor 8 (PI8), containing two instances of the minimal furin recognition sequence (VVRNSRCSRM$^{343}$) (SEQ ID NO 9), has been shown to form SDS-stable complexes with furin with an overall $K_i$ of 53.8 pM. However, the inhibition of furin by PI8 in vivo, or indeed the co-localization of PI8 and furin within the secretory pathway, has not yet been demonstrated. Due to its size, one would expect this proteinase inhibitor to be immunogenic.

The only naturally occurring intracellular furin inhibitor that has been described to date is furin's own propeptide. The prodomains of proteases often play a role in the activation and regulation of activity of their cognate enzymes. It has been reported that furin is efficiently inhibited by a GST-furin propeptide fusion construct, and that furin prosegments expressed intracellularly can act in trans to inhibit substrate processing.

The therapeutic value of furin inhibitors was recently highlighted by a report showing that exogenous application of the large protein α1-PDX would block in vivo maturation of pro-gB, the human cytomegalovirus envelope glycoprotein. As uptake of α1-PDX into the cell could not be detected in cell lines lacking the enzyme, it was suggested that α1-PDX bound to furin at the cell surface. *Pseudomonas* exotoxin A activation has also been prevented by extracellular application of α1-PDX to A7 melanoma cells, as has the processing of HIV-1 glycoprotein gp160 in transfected cells. These studies demonstrate that the selective inhibition of furin can inhibit pathological disease processes. Inhibition of furin can occur on the extracellular surface rather than in the interior of the cell. It is difficult to obtain α1-PDX in high yield. Due to its size, antitrypsin Portland would be expected to be immunogenic. See F. Jean et al., *Proc. Natl. Acad. Sci. USA*, vol. 95, pp. 7293-7298 (1998).

T. Komiyama et al., "Engineered eglin c variants inhibit yeast and human proprotein processing proteases, Kex2 and furin," *Biochem.*, vol. 39, pp. 15156-15165 (2000) reported that certain eglin-based variants would inhibit furin. Due to its size, one would expect the eglin protein to be immunogenic.

Previously reported small molecules that inhibit furin exhibit toxicity at the concentrations needed for inhibition. For example, previously reported inhibitors include decanoyl-RVKR-CH$_2$-AVG-NH$_2$ with a Ki of 3.4 nM, ketomethylenes with $K_i$'s in the low micromolar range, and the octapeptidyl chloromethane derivative Ac-YEKERSKR-CH$_2$Cl with a low nM $K_i$ for both PC1 and furin. However, ketones and chloromethane derivatives tend to have unacceptable in vivo toxicity; hence their use has largely been confined to probing enzyme-structure relationships in vitro. See, e.g., S. Hallenberger et al., *Nature*, vol. 360, pp. 358-361 (1992).

In contrast, polyarginines have been used in vivo for other purposes without apparent cytotoxicity, including studies of mucin release in goblet cells, activation of phospholipase D, and mimicking the cationic major basic protein. See K. Ko et al., *Am. J. Physiol.*, vol. 277, pp. L811-L815 (1999); S. Vepa et al., *Am. J. Physiol.*, vol. 272, pp. L608-L613 (1997); A. Coyle et al., *Am. J. Respir. Crit. Care Med.*, vol. 150, pp. S63-S71 (1994); and E. Frigas et al., *Mayo Clin. Proc.*, vol. 56, pp. 345-353 (1981). No prior report has suggested that polyarginines should have anti-furin activity.

L- and D-polyarginines with six or more amino acid residues have been reported to enter cells more efficiently than polymers of equal length formed of lysine, ornithine, and histidine. See D. Mitchell et al., "Polyarginine enters cells more efficiently than other polycationic homopolymers," *J. Peptide Res.*, vol. 56, pp. 318-325 (2000).

There is an unfilled need for furin inhibitors that combine the characteristics of high potency, high stability, high specificity, low toxicity, and low molecular weight.

We have discovered small peptides that strongly inhibit, that are stable, and that have low molecular weight. These peptides are polybasic peptides, e.g. hexa- to nona-peptides having Arg or Lys in most or all positions. We also found that removing the peptide terminating groups can improve inhibition of furin. The most potent inhibitor tested to date, nona-L-arginine (SEQ ID NO 13), had a $K_i$ against furin of 42 nM. Non-acetylated, poly-D-arginine-derived molecules, e.g., hexa-D-arginine, are preferred furin inhibitors for therapeutic uses, such as inhibiting certain bacterial infections, viral infections, and cancers. Due to their relatively small size, the peptides used in this invention should be non-immunogenic. These peptides are efficiently transported across cell membranes.

BRIEF DESCRIPTION OF THE DRAWINGS

FIG. 1(*b*) depicts a representative chromatogram after the fractions containing the peak enzyme activity were pooled.

FIGS. 4(*a*) through 4(*l*) depict the inhibition of furin by various L-hexapeptides.

FIGS. 5(*a*) through 5(*f*) depict the inhibition of furin by various D-hexapeptides.

FIGS. 10(*a*) through (*h*) depict the cleavage of nona-L-arginine (SEQ ID NO 13) and hexa-L-arginine (SEQ ID NO 14) by furin.

EXPERIMENTAL PROCEDURES

Figure 1A:
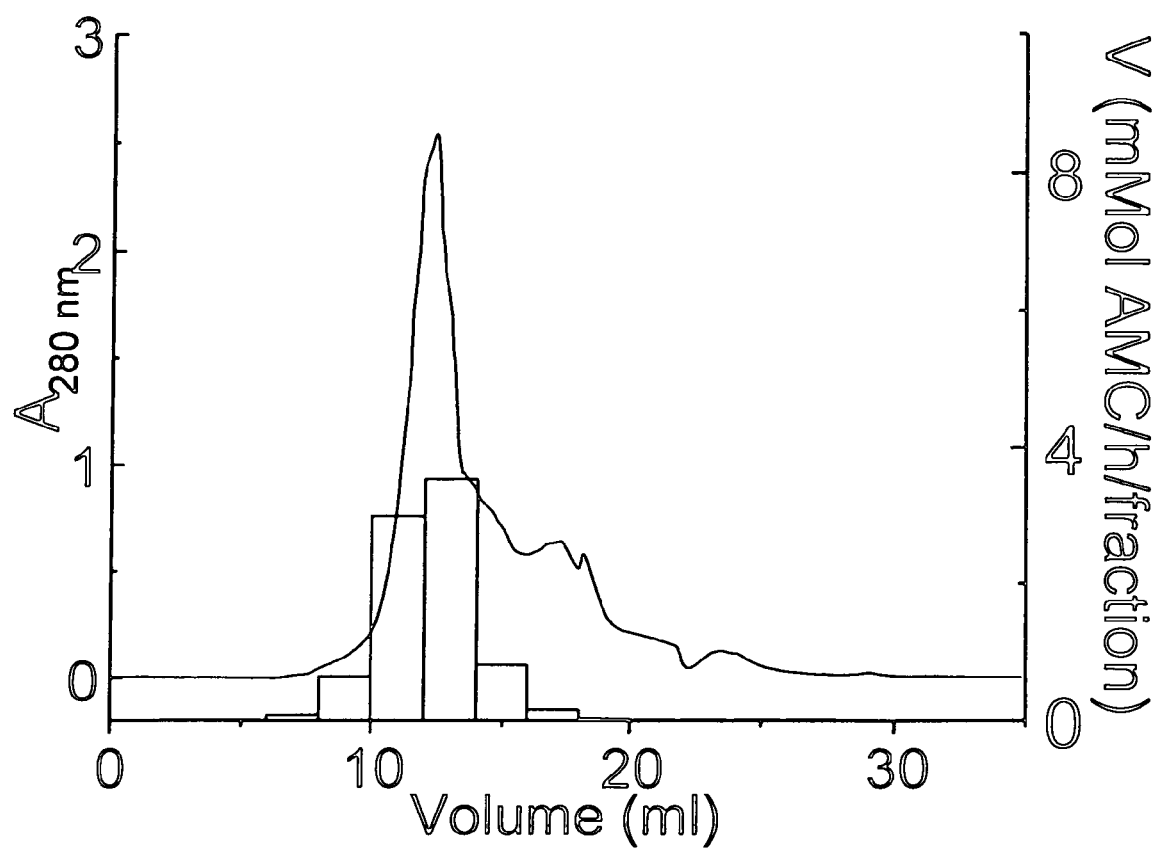
FIG. 1(*a*) depicts the results of the purification of recombinant furin. The figure shows elution volume from the start of the salt gradient.

Materials. Hexapeptide libraries and synthetic peptides were synthesized at the Torrey Pines Institute for Molecular Studies (San Diego, Calif.). Two positional scanning hexapeptide libraries were screened for inhibition of furin, one made up solely of L-amino acids and the other solely of D-amino acids. Each hexapeptide library comprised 120 peptide mixtures with amino-terminal acetylation and carboxyterminal amidation, divided into six groups corresponding to each position within the hexapeptide. For each position, 20 mixtures were surveyed, each of which was defined by one of the twenty natural amino acids. The undefined positions were occupied by any of the amino acids except cysteine. The positional scanning libraries and the individual compounds were synthesized using simultaneous multiple peptide synthesis methods known in the art. The L-polyarginine synthesis was performed by the Louisiana State University Health Sciences Center Core Laboratories; mass spectroscopy was used to verify identities of the peptides. The α1-PDX was a generous gift from G. Thomas, Portland, Oreg. The anti-furin antiserum, MON148, was a kind gift from W. Van de Ven, Leuven, Belgium. Anti-Myc and anti-His antisera were obtained from Invitrogen (Carlsbad, Calif.). The pERTKR-MCA was obtained from Peptides International (Louisville, Ky.). N-Glycosidase F was obtained from Calbiochem (La Jolla, Calif.).

Recombinant convertase preparation. The mouse furin clone was a kind gift from K. Nakayama (Fukuoka University School of Medicine, Fukuoka, Japan). The mouse furin cDNA was truncated N-terminally to the transmembrane domain at $His^{711}$ using PCR. This PCR product was then subcloned into pcDNA3.1 (−) myc-His (Invitrogen) at the Nhe1 and Xba1 restriction sites. Dihydrofolate-reductase-negative DG44 Chinese Hamster Ovary (CHO) cells (L. Chasin, Columbia University, New York, N.Y.) were transfected using Lipofectin (Life Technologies), and colonies were selected at 37° C. in 5% $CO_2$ in α-MEM (lacking nucleosides) containing 10% well-dialyzed fetal bovine serum (Life Technologies). Conditioned media from colonies were screened using an enzyme assay (see below), and a high-expressing clone was selected. Overexpression of furin was achieved by increasing the methotrexate concentration from 5 nM to 50 μM in five- to ten-fold steps as described in I. Lindberg et al., *Methods Neurosci.*, vol. 23, pp. 94-108 (1995). The amplified lines were tested for increased furin expression by enzyme assay. Once the 50 μM methotrexate level had been reached, cells were split at ratios of 1:6 twice a week. 100 mL of conditioned media (OptiMEM, Life Technologies) containing 100 μg/mL aprotinin (Miles Laboratories, Kankakee, Ill.) was collected from confluent roller bottles every 24 h. The medium was then centrifuged at low speed to remove cells, and the supernatant was stored at −80° C. until use.

Purification of furin: Conditioned medium was thawed, pooled, and diluted 1:3.5 with buffer A (20 mM HEPES, 0.1% Brij 35, 5 mM $CaCl_2$, pH 7.4), and pumped at 40 mL/min through a Sartorius D100 anion exchange membrane. The membrane was washed with 40 mL of buffer A, followed by 40 mL of buffer A containing 50 mM NaCl, and finally by 40 mL of buffer A containing 200 mM NaCl. The fraction eluting with 200 mM NaCl was diluted 1:4 with buffer A and applied to a 1 mL Pharmacia Mono Q HR5/5 anion exchange column at a flow rate of 1 mL/min. Following a 10 mL wash with buffer A, furin was eluted by a linear increase of 0 to 500 mM NaCl in buffer A over 30 mL; and 2 mL fractions were collected. Fractions containing peak activity were pooled, and 200 µL aliquots were subjected to gel permeation chromatography using a Pharmacia Superose 12 column at a flow rate of 0.5 mL/min of buffer A containing 200 mM NaCl. Fractions were assayed for activity as described below; protein content was determined using the Bradford method. All purification steps were performed at 4° C.

Alternatively, the enzyme-containing fraction eluting from the ion-exchange membrane with 200 mM NaCl was pumped onto a 1 mL Ni-NTA Superflow (Qiagen) column at 0.3 mL/min, washed with 10 mL of buffer A, and then eluted with a two-step gradient of 0-20 mM imidazole in buffer A over 20 mL, followed by a linear gradient of 20 to 200 mM in imidazole in buffer A. The fractions containing peak enzymatic activity were pooled and subjected to ion exchange chromatography with a Mono Q column as described above.

The proprotein convertases PC1 and PC2 were prepared by ion exchange chromatography as described in G. Frenette et al., *Biochim. Biophys. Acta.*, vol. 1334, pp. 109-115 (1997).

The proprotein convertase PACE4 was partially purified from an overnight-conditioned medium of stably transfected hEK-293 human embryonic kidney cells (a generous gift of R. E. Mains, Johns Hopkins University School of Medicine, Baltimore, Md.). Briefly, 100 mL of conditioned medium (OptiMEM containing 100 µg/mL aprotinin) was loaded onto an Econo-Pac Q (Bio-Rad) column at 4 mL/min, washed with 10 mL of buffer A, and then eluted with a linear gradient of buffer A containing 500 mM NaCl over 50 mL. The active fractions were then diluted 1:4 with buffer A prior to loading onto a Mono Q column (Pharmacia) at 1 mL/min. The PACE4 was eluted with a linear gradient of buffer A containing 500 mM NaCl over 10 mL. The resulting active fractions were then pooled and stored at −80° C. until use. The validity and purity of the preparation were verified using Coomassie staining and Western blotting with a polyclonal anti-PACE4 antiserum (a gift of R. E. Mains, Johns Hopkins University School of Medicine, Baltimore, Md.).

Enzyme Assays and Hexapeptide Library Screening. Enzyme assays for PC1 and PC2 were performed at pH 5.0 using pERTKR-MCA (Peptides International Inc., Louisville, Ky.) as described in E. Apletalina et al., *J. Biol. Chem.*, vol. 273, pp. 26589-26595 (1998). The assay for furin was performed using the same substrate at pH 7.0 in 100 mM HEPES, 5 mM $CaCl_2$, 0.1% Brij 35. All assays were performed at 37° C. in a 96 well fluorometer (Labsystems) at an excitation wavelength of 380 nm with emission monitored at a wavelength of 460 nm. The total volume was 50 µL. Unless otherwise stated, the final substrate concentration for all assays was 200 µM. When used in a particular experiment, the inhibitory peptides were pre-incubated with enzyme for 30 min at room temperature prior to addition of substrate. All assays were performed in duplicate or triplicate. Inhibition constants were determined using the method of Apletalina et al. (1998), and the equation $K_i = K_{i(app)}/(1+([S]/K_m))$. The $K_m$s of PC1, PC2, furin, and PACE4 were determined as 11, 42, 8, and 15 µM, respectively, using a computerized least squares fitting technique with EnzFitter (BioSoft, Cambridge, England).

Digestion of recombinant furin with N-Glycosidase F. A 200 µL aliquot of the pooled fractions from the Superose chromatography (containing 40 µg of furin) was made up to 4.5% beta mercaptoethanol, 0.45% SDS and boiled for ten minutes prior to concentration to 60 µL using a Centricon 10 (Amicon). The concentrate was diluted to 400 µL using 50 mM sodium phosphate buffer, pH 7.5, 0.76% Triton X-100; and 1.8 µg of N-Glycosidase F (Calbiochem) was added. The sample was incubated at 37° C., and 45 µL aliquots were removed at the times indicated and placed in 5 µL of 5×SDS buffer prior to boiling for 3 min. The aliquots were separated by SDS-PAGE (8.8%) and visualized with Coomassie blue staining.

Cleavage of Nona-L-arginine and Hexa-L-arginine by Furin. Nona-L-arginine (200 µM) (SEQ ID NO 13) or hexa-L-arginine (200 µM) (SEQ ID NO 14) was incubated at 37° C. with or without furin (1.7 µM), in 100 mM HEPES, pH 7 containing 5 mM $CaCl_2$ and 0.2% Brij 35. Aliquots (20 µL) were removed at the indicated times, placed into 480 µL ice-cold 0.1% TFA, immediately frozen and kept frozen until HPLC analysis. After thawing, the aliquots were separated on a 5 µm, 0.46×25 cm Beckman (Fullerton, Calif.) ODS column with a linear gradient of 0 to 15% acetonitrile containing 0.1% trifluoroacetic acid over 40 min at 1 mL/min. Absorbance was monitored at 214 nm. Cleavage products were identified by comparison to polyarginine standards. Parallel reactions containing buffer instead of furin were also analyzed.

Results

Overexpression, Purification, and Characterization of Recombinant Mouse Furin. The use of the dihydrofolate reductase-coupled amplification method to overexpress truncated furin produced a cell line that secreted roughly 0.8 µg/mL furin into the culture medium, as estimated by the specific activity of the purified protein. As shown in Table 1, the initial ion exchange step, while having a relatively low yield, nevertheless proved valuable as a method of rapidly concentrating the conditioned medium from a large volume, while at the same time removing phenol red and contaminating protein from the product. After the volume was thus reduced, it was then possible to load the high resolution Mono Q (Pharmacia) ion exchange column used in the second ion exchange step within a reasonable time.

FIG. 1(*a*) depicts the results of the purification of the recombinant furin. Partially purified, concentrated recombinant mouse furin from the first ion exchange step was diluted 1:4 with buffer A and pumped through a MONO Q HR5/5 column (Pharmacia) equilibrated with buffer A. The column was washed with 5 mL of buffer A before elution with a 30 mL gradient of 0 to 500 mM NaCl in buffer A. The figure shows elution volume from the start of the salt gradient.

FIG. 1(*b*) depicts a representative chromatogram after the fractions containing the peak enzyme activity were pooled and the aliquots applied to a Superose 12 column. The bars depict activity against pERTKR-MCA. The solid line depicts UV absorbance at 280 nm. The gel permeation column was calibrated with the molecular weight standards marked as □: thyroglobulin, 670 kDa; IgG, 150 kDa; ovalbumin, 44 kDa; myoglobin, 17 kDa; cyanocobalamin, 1.35 kDa. (All molecular weight standards were obtained from Biorad).

As can be seen in FIG. 1(*a*), the majority of the protein eluted as a single peak, coincident with the proprotein convertase activity. Again, the yield from this step was low, but an appreciable increase in specific activity was observed. See Table 1.

TABLE I

Purification of Recombinant Furin

| Purification Step | Total Activity (Units[a]) | Total Protein (mg) | Specific Activity (units/mg) | Yield (%) | Purification Factor |
|---|---|---|---|---|---|
| Conditioned Medium | 156 | 54 | 2.9 | (100) | (1) |
| Ion Exchange 1 | 84 | 7.6 | 11 | 54 | 3.8 |
| Ion Exchange 2 | 46 | 2.4 | 19 | 29 | 6.7 |
| Gel Permeation | 42 | 2 | 21 | 27 | 7.2 |

[a]1 Unit = 1 μmol aminomethylcoumarin/hour

Figure 1B:
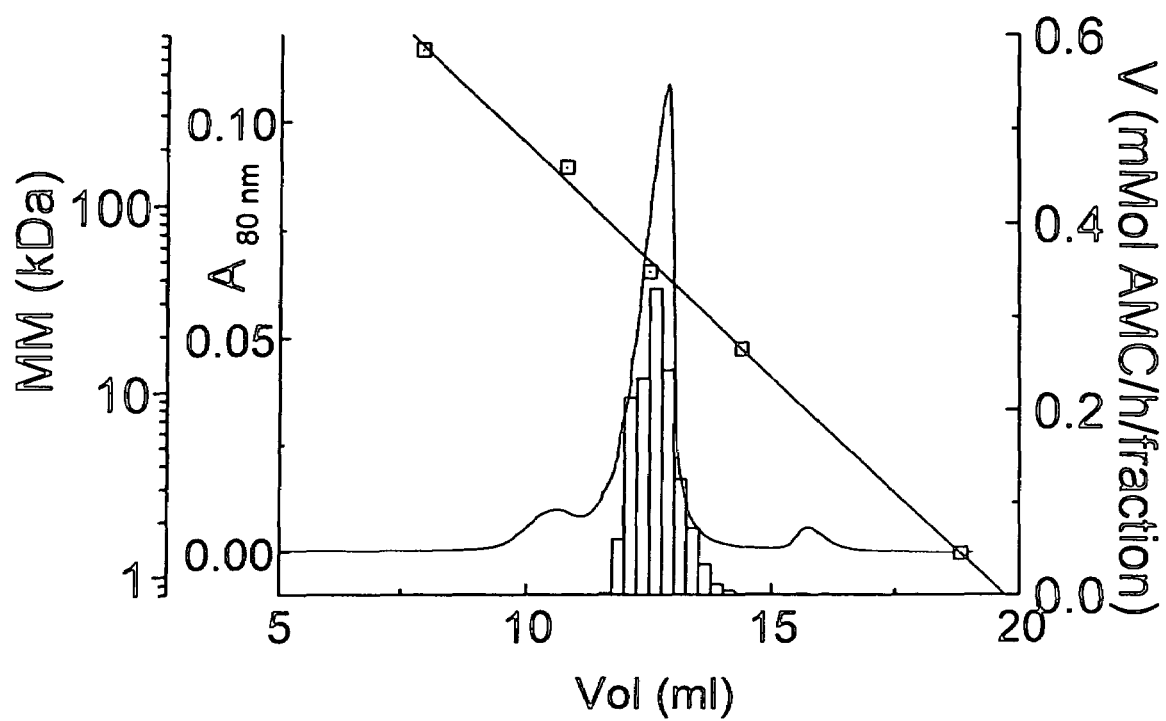

The fractions with maximum activity were pooled and subjected to gel permeation chromatography, as shown in FIG. 1(b). In this step virtually all the protein eluted as a single peak, with only small amounts eluting at lower and higher molecular weights. The furin activity exactly coincided with the major absorbance peak. The fractions having maximum activity were pooled, diluted with glycerol to a final concentration of 10%, and stored at −80° C. until use. Under these conditions there was no detectable loss in activity over six months. Molecular weight standards used to calibrate the gel permeation column indicated a molecular weight for furin of about 59 kDa. Coomassie Blue staining and Western blotting (data not shown) of the gel permeation-purified fractions revealed a single band at 61 kDa. The final specific activity was 21 Units/mg protein; and the overall yield for the purification was 27%, with a purification factor of 7.2.

We had initially attempted purifications using a C-terminally located hexa-His (SEQ ID NO 15) tag as a ligand for affinity chromatography with a metal ion chelation resin (Ni-NTA Superose, Qiagen). However, the furin activity then eluted at very low (~20 mM) imidazole concentrations, with no increase in specific activity compared with the sample applied. Subsequent Western blotting with both anti-His and anti-Myc antisera (Invitrogen) showed no immunoreactivity, whereas blotting using the anti-furin antiserum Mon148 (a generous gift of W. Van de Ven, University of Leuven, Leuven, Belgium) revealed a strong band at 61 kDa (not shown), indicating that C-terminal truncation of the secreted product had occurred. The metal ion chelation step was subsequently abandoned and all other data presented here were obtained using furin purified using ion exchange and gel permeation chromatography as otherwise described above.

Treatment of the purified furin with N-glycosidase F revealed the presence of two lower molecular weight forms, indicating that two of the three potential sites in the recombinant furin preparation were present and originally glycosylated.

Figure 2:
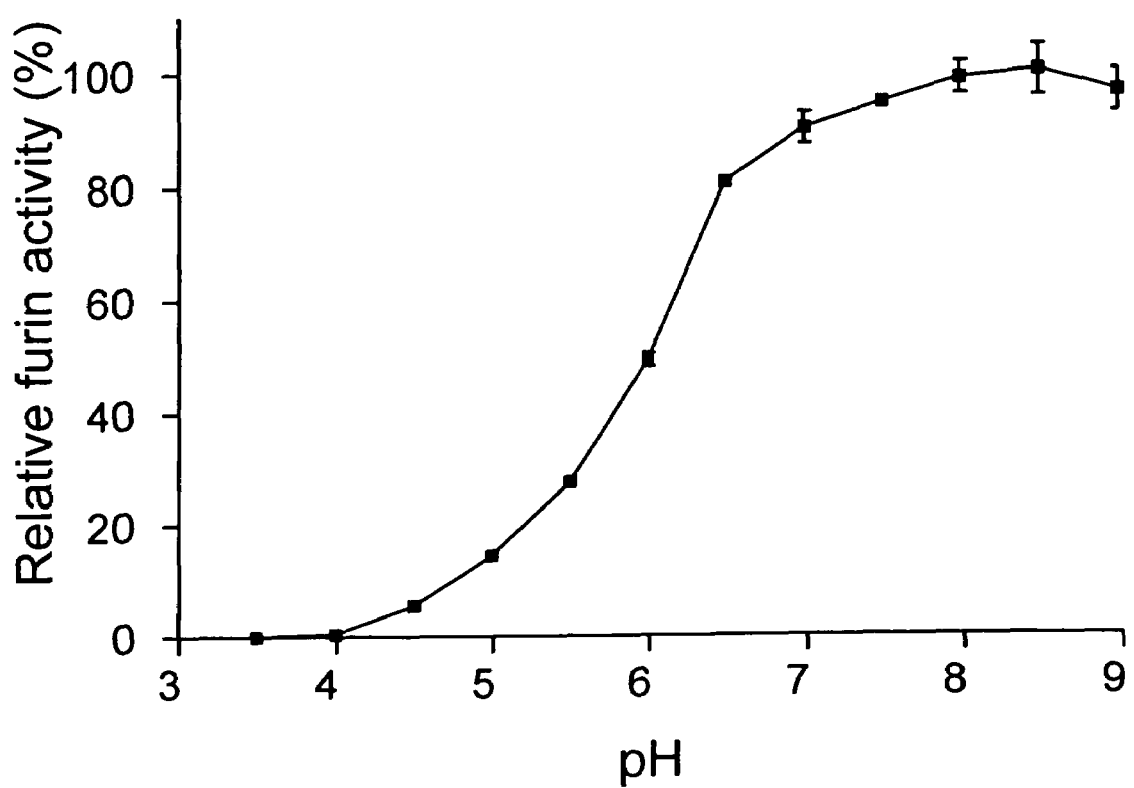
FIG. 2 depicts the effect of pH on furin activity.
Figure 3:
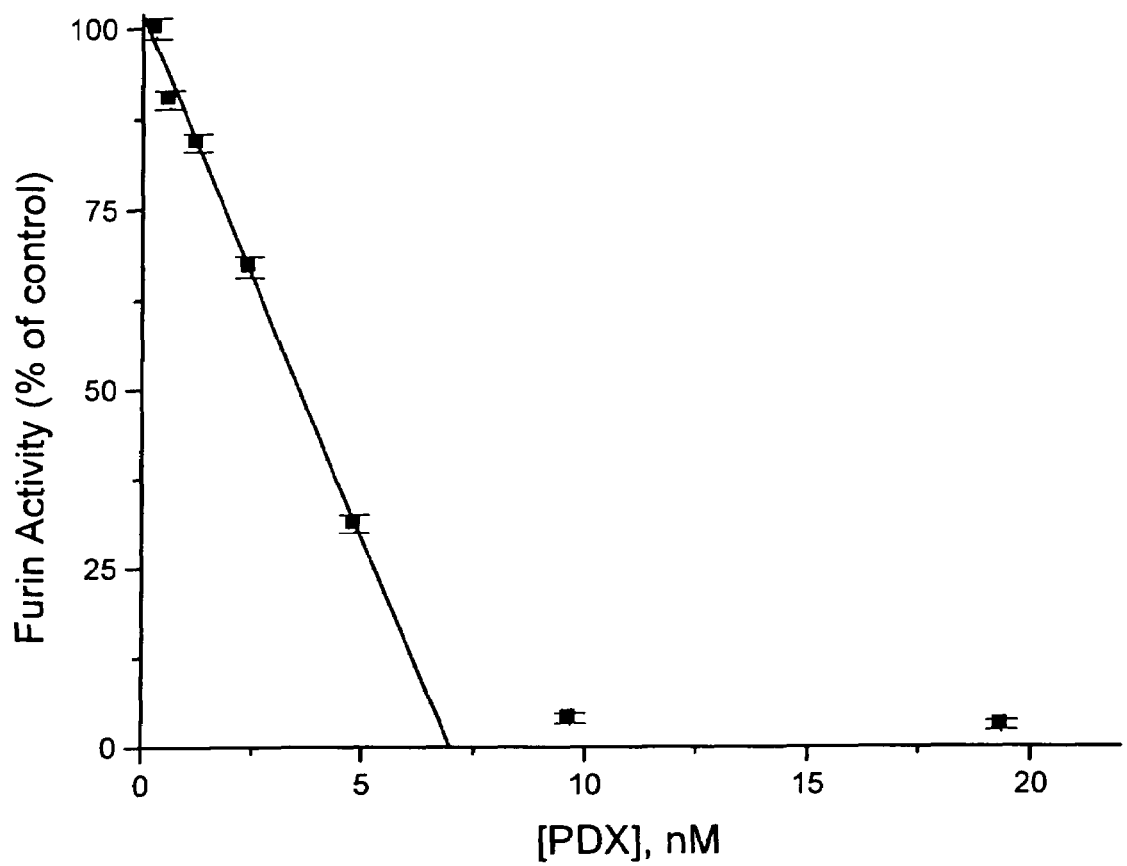
FIG. 3 depicts the inhibition of furin at nanomolar α1-PDX concentrations.

FIG. 2 depicts the effect of pH on furin activity. While there was a rapid drop in activity below pH 6.5, the enzyme retained greater than 90% of maximum activity at pH 9.0. Calcium concentrations over 1 mM were required for full activity, with no significant difference in activity as calcium concentrations were increased thereafter to 50 mM. Consistent with previous reports, as shown in FIG. 3, furin was strongly inhibited at nanomolar α1-PDX concentrations, giving further validation of the enzyme preparation.

L-Hexapeptide Library Scan. To identify amino residues playing a significant role in the inhibition of furin, we screened a positional scanning L-hexapeptide library (amino terminally acetylated and carboxy terminally amidated) using the standard enzyme substrate pERTKR-MCA (i.e., pyr-Glu-Arg-Thr-Lys-Arg-methylcoumarinamide). In total, the library was screened nine times, at inhibitor concentrations of 1.0 and 0.5 mg/mL, and at substrate concentrations of 200 and 100 μM. The concentrations of inhibitor and substrate were found to influence the degree of observed inhibition. Screening at the lower substrate concentration gave better discrimination between peptides bearing different residues at all inhibitor concentrations. In addition, at the lower substrate concentration, better discrimination was shown for positions P1, P2 and P3 at 1 mg/mL inhibitor concentration (FIGS. 4(a)-(f)), while better discrimination for positions P4, P5 and P6 was seen at 0.5 mg/mL inhibitor concentration (FIGS. 4(g)-(l)).

FIGS. 4(a) through 4(l) depict the inhibition of furin by various L-hexapeptides. Each peptide mixture was pre-incubated with furin in assay buffer for 30 min prior to the addition of substrate (final concentration, 100 μM). The rate of hydrolysis of pERTKR-MCA was followed for 1 hour. Inhibition is given as the percentage decrease in activity in the presence of the peptide mixture relative to that of control. In FIGS. 4(a) through 4(f), the peptide concentration was 1 mg/mL. In FIGS. 4(g) through 4(l), the peptide concentration was 0.5 mg/mL.

From FIGS. 4(a)-(f) (i.e., the experiments using an inhibitor concentration of 1 mg/mL) it can be seen that at position P1, Arg, Lys and His exerted greater than average inhibition, while at positions P2 and P3, Arg and Lys, but not His, were the preferred residues. At positions P4, P5 and especially at position P6, many residues showed greater than average inhibition, but no clear distinction could be made on either the basis of size, hydrophobicity or charge. In contrast, at the lower 0.5 mg/mL inhibitor concentration (FIGS. 4(g)-(l)), while there were no clearly preferred residues at positions P1, P2 or P3, there was good discrimination at positions P4, P5 and P6. On the basis of the screens shown in FIG. 4, we selected Arg in positions P1, 2 and 3, Lys in P4; His or Arg in P5; and His, Met, Lys or Arg in P6 for assembly into discrete peptide sequences.

D-Hexapeptide Library Scan. The positional scanning acetylated and amidated D-hexapeptide library was screened a total of nine times at either 0.5 mg/mL or 1.0 mg/mL inhibitor and either 50 μM or 100 μM substrate concentration; in all cases the results were similar. A representative screen is shown in FIGS. 5(a)-(f).

FIGS. 5(a) through 5(f) depict the inhibition of furin by various D-hexapeptides. Each peptide mixture (final concentration, 1 mg/mL) was pre-incubated with furin in assay buffer for 30 min prior to the addition of substrate (final concentration, 100 μM). The rate of hydrolysis of pERTKR-MCA was followed for 1 hour. Inhibition is given as the percentage decrease in activity in the presence of the peptide mixture relative to that of control.

While D-Arg was one of the preferred residues in all positions, the remainder of the inhibitory residues were hydrophobic. Interestingly, D-Lys effected greater than average inhibition only in position P6, but still showed less inhibition than the most effective residue, D-Trp. In positions P3, P4, and P5, D-Arg was marginally the most potent residue when all results were averaged. In position P2, D-Arg and D-Ile consistently produced relatively high inhibition, while the same was true for D-Arg and D-Leu in position P1. In all cases relative inhibition values were consistently lower than those of the L-hexapeptide library, indicating a preference of furin for L-residues. Nevertheless, a series of D-hexapeptides was synthesized based upon the results described above, in which position P1 was either D-Arg or D-Leu, P2 was either D-Arg or D-Ile, positions P3, P4 and P5 were always D-Arg, and P6 was always D-Trp.

Figure 6A:
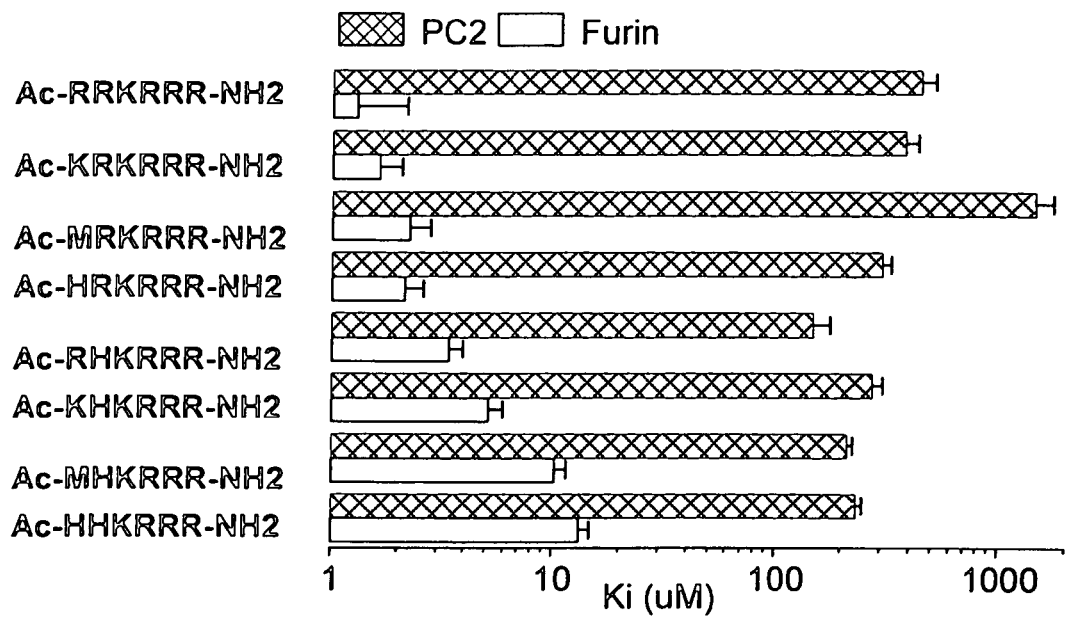
FIGS. 6(*a*) and 6(*b*) depict the $K_i$'s of amidated and acetylated D- and L-hexapeptides against both furin and P2. The peptides mentioned in FIG. 6(*a*) are, from bottom to top, SEQ ID NO 16, SEQ ID NO 17, SEQ ID NO 18, SEQ ID NO 19, SEQ ID NO 20, SEQ ID NO 21, SEQ ID NO 22, and SEQ ID NO 23.
Figure 6B:
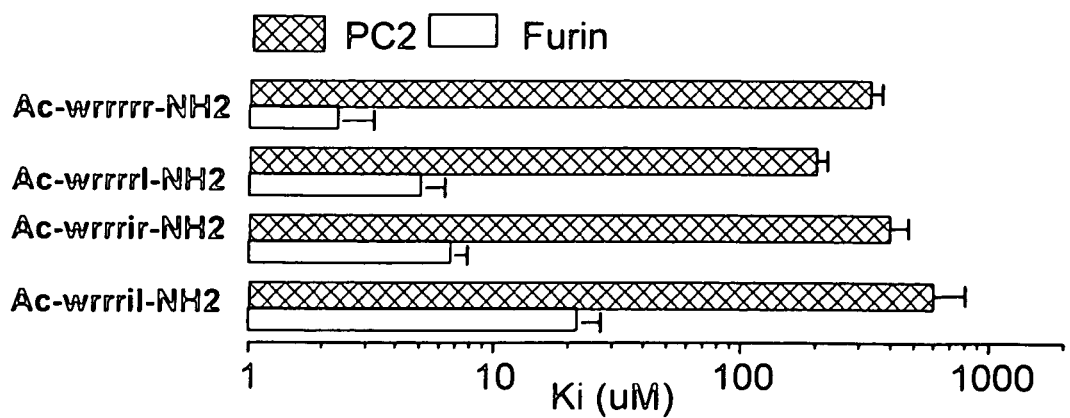

Inhibition of Furin and PC2 by Synthetic Peptides. The amidated and acetylated D- and L-hexapeptides that were synthesized based on the results of the D- and L-hexapeptide library screens were tested against both furin and PC2. For both the D- and L-peptide series, the $K_i$'s against furin were all in the low μM range; these peptides all inhibited furin ~10-100 times more strongly than they inhibited PC2. (See Table 2 and FIGS. 6(a) and 6(b)). Against furin, the potency increased as the sequence became more basic, an observation that did not hold for PC2. Examination of the $K_i$'s of the L-hexapeptides against furin revealed that in position 5, Arg was preferred to His, and that the inhibitory potency of these peptides against furin increased as P6 was changed in the order His, Met, Lys, Arg. The same order of inhibitory potency was not seen against PC2: in this instance His was preferred to Arg in P5. While the combination of a P5 Arg and a P6 Met was severely unfavorable as a PC2 inhibitor, when used against furin the influence of the P5 residue appeared to outweigh that of the P6 residue.

The D-hexapeptide inhibitors were also assayed against furin and PC2 (Table 2). Against furin, D-Arg was preferred to D-Ile in P2, and D-Arg was preferred to D-Leu in P1. However, the presence of a basic residue at P1 or P2 was sufficient to produce a relatively potent furin inhibitor, despite the presence of a hydrophobic residue at P2 or P1. Conversely, when D-Arg was present at P2, substituting D-Leu for D-Arg in P1 produced a more potent PC2 inhibitor. Thus, like the L-peptide inhibitors, increasing basicity resulted in a more potent furin inhibitor, but not a more potent PC2 inhibitor.

TABLE 2

Inhibition constants of various L- and D-hexapeptides against furin and PC2[b]

| | $K_i$ (μM) | |
|---|---|---|
| | Furin | PC2 |
| L-Peptides | | |
| Ac-HHKRRR-NH$_2$ (SEQ ID NO 16) | 13.2 ± 1.6 | 235 ± 16 |
| Ac-MHKRRR-NH$_2$ (SEQ ID NO 17) | 10.3 ± 1.4 | 216 ± 13 |
| Ac-KHKRRR-NH$_2$ (SEQ ID NO 18) | 5.2 ± 0.9 | 280 ± 29 |
| Ac-RHKRRR-NH$_2$ (SEQ ID NO 19) | 3.4 ± 0.6 | 152 ± 30 |
| Ac-HRKRRR-NH$_2$ (SEQ ID NO 20) | 2.1 ± 0.5 | 309 ± 29 |
| Ac-MRKRRR-NH$_2$ (SEQ ID NO 21) | 2.3 ± 0.5 | 1,500 ± 300 |
| Ac-KRKRRR-NH$_2$ (SEQ ID NO 22) | 1.6 ± 0.5 | 391 ± 60 |
| Ac-RRKRRR-NH$_2$ (SEQ ID NO 23) | 1.3 ± 0.9 | 461 ± 75 |
| D-Peptides | | |
| Ac-wrrril-NH$_2$ | 22.7 ± 4.3 | 601 ± 200 |
| Ac-wrrrir-NH$_2$ | 7.0 ± 0.9 | 399 ± 75 |
| Ac-wrrrrl-NH$_2$ | 5.3 ± 1.0 | 203 ± 20 |
| Ac-wrrrrr-NH$_2$ | 2.4 ± 0.8 | 334 ± 37 |

[b]The rate of hydrolysis of pERTKR-MCA was determined in the presence of various concentrations of the different peptides as described in the experimental procedures. The results obtained were then used to compute the $K_i$ values for the peptides. Each value represents the mean ± S.D. determined from three independent experiments.

Figure 7B:
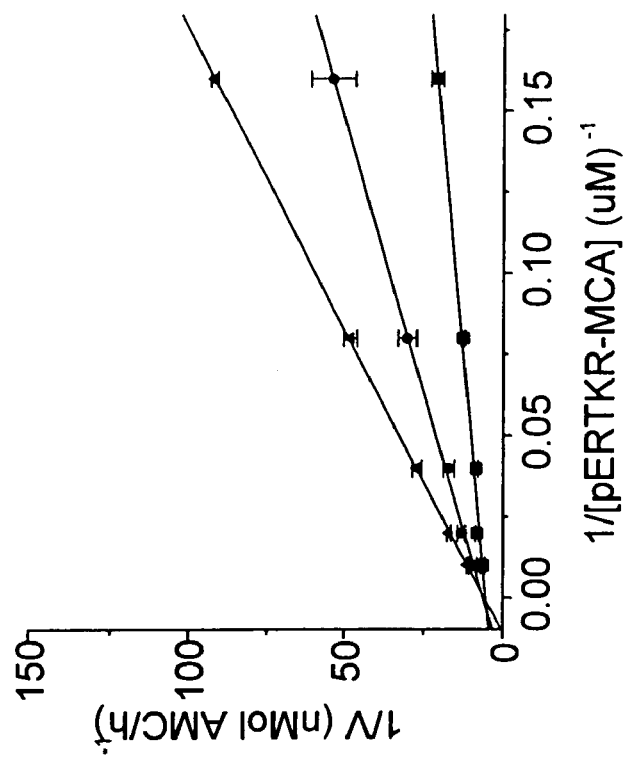
FIGS. 7(*a*) and (*b*) depict Lineweaver-Burk plots of the most potent L- and D-hexapeptides identified from the library screens.
Figure 7A:
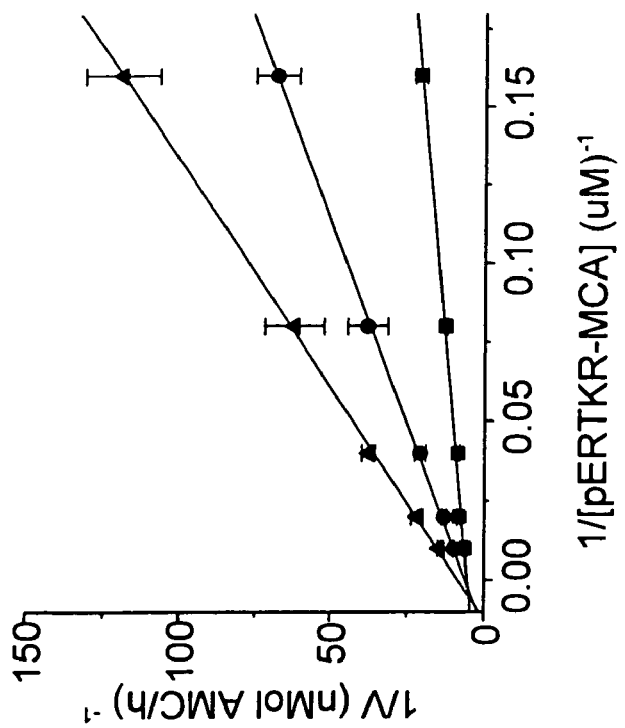

Mechanism of Inhibition. FIGS. 7(a) and (b) depict Lineweaver-Burk plots of the most potent L- and D-hexapeptides identified from the library screens. Furin (30 nM) was preincubated in 100 mM HEPES, 5 mM CaCl$_2$, 0.1% Brij 35, pH 7.0 with either 0 (□), 20 (○) or 40 (Δ) μM of Ac-RRKRRR-NH$_2$ (FIG. 7(a)) (SEQ ID NO 23) or of Ac-wrrrrr-NH$_2$ (FIG. 7(b)) prior to addition of substrate at the final concentrations indicated. The results demonstrated strictly competitive-type inhibition for both the L- and D-peptides. No deviation was seen from classical Michaelis-Menten-type kinetics, typical of tight binding or suicide inhibitors such as displayed by α1-PDX and the chloromethyl derivatives, both of which function by forming an irreversible complex with the enzyme.

Figure 8:
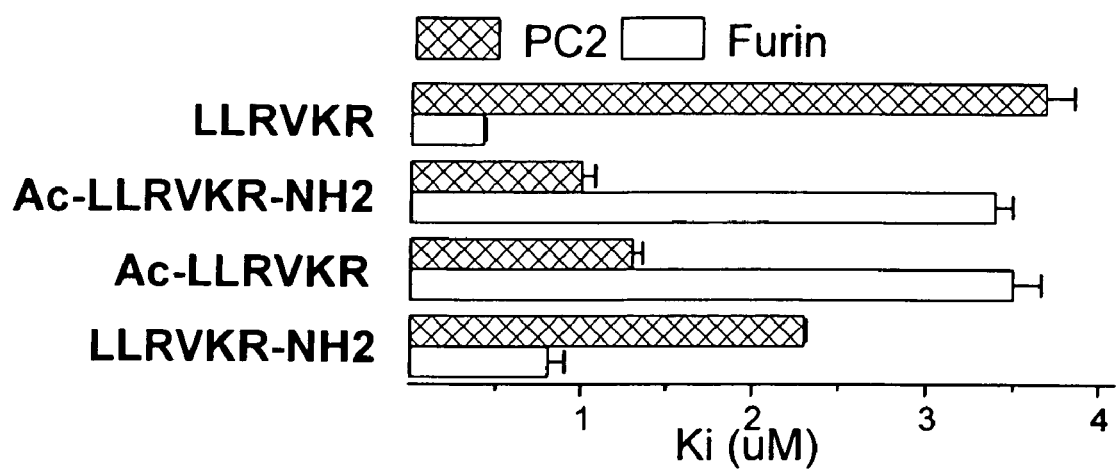
FIG. 8 depicts the effects of the terminal acetyl and amide modifications on inhibitory potency. The peptides mentioned in FIG. 8 are SEQ ID NO 24, and modifications of SEQ ID NO 24, with and without N-terminal acetylation, C-terminal amidation, or both.
Figure 9A:
FIGS. 9(*a*)-(*d*) depict the effect of chain length on the inhibitory properties of L-polyarginine peptides having from 4 to 9 arginine residues. The peptides mentioned in each of FIGS. 9(*a*)-(*d*) are SEQ ID NO 25, SEQ ID NO 26, SEQ ID NO 14, SEQ ID NO 27, SEQ ID NO 28, and SEQ ID NO 13.
Figure 9B:
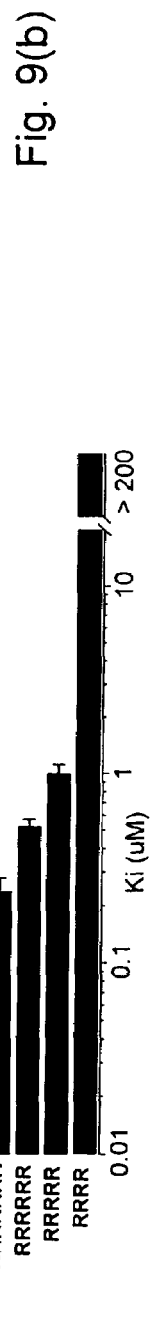
Figure 9C:
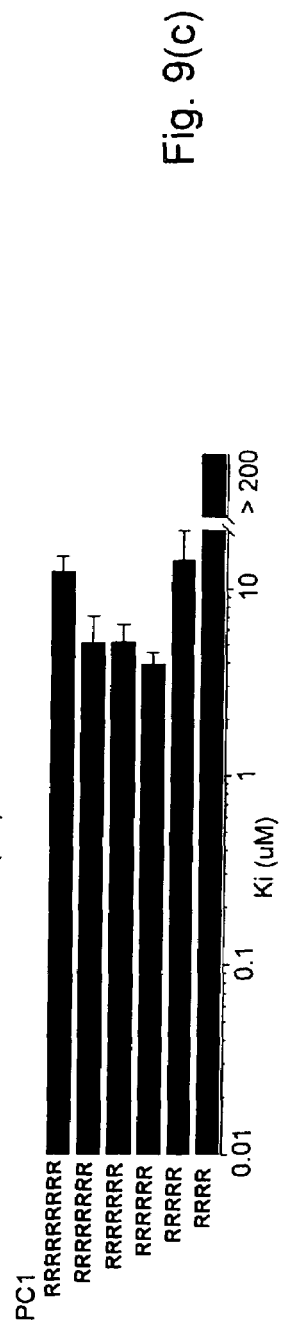
Figure 9D:
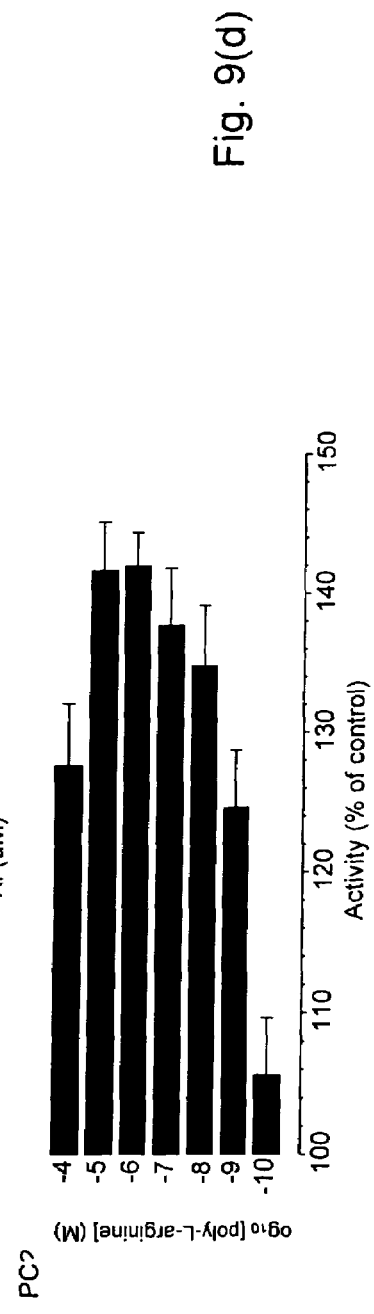

The Effect of N-Terminal Acetyl and C-Terminal Amide Groups on Inhibition. We also examined the effect of the terminal acetyl and amide modifications on inhibitory potency. Initially, various forms of an amidated and acetylated L-hexapeptide, LLRVKR (SEQ ID NO 24), previously identified by Apletalina et al. (1998) as a nanomolar inhibitor of PC1, were tested against furin and PC2. The results are shown in Table 3 and FIG. 8. Interestingly, removing the terminal amide and acetyl groups from this hexapeptide increased its inhibitory potency against furin eight-fold. It appeared that the relative lack of inhibitory potency of the unacetylated and unamidated peptide against furin was almost solely attributable to the N-terminal acetyl group. In contrast, when the same peptides were tested against PC2, the terminating groups appeared to assist in inhibition. The $K_i$ of the acetylated and amidated peptide was nearly four-fold smaller against PC2 than the $K_i$ of the unmodified peptide. Comparing peptides, it was seen that removing the N-terminal acetyl group resulted in the loss of inhibitory potency against PC2, implying that PC2 has sequence recognition ability that extends beyond the P6 side chain.

TABLE 3

The effect of N-terminal acetylation and C-terminal amidation on the inhibition of furin and PC2[c] by SEQ ID NO 24

| | Ki (μM) | |
|---|---|---|
| | Furin | PC2 |
| LLRVKR-NH$_2$ | 0.8 ± 0.1 | 2.3 ± 0.2 |
| Ac-LLRVKR | 3.5 ± 0.2 | 1.3 ± 0.6 |
| Ac-LLRVKR-NH$_2$ | 3.4 ± 0.1 | 1.0 ± 0.08 |
| LLRVKR | 0.42 ± 0.02 | 3.7 ± 0.17 |

[c]The rate of hydrolysis of pERTKR-MCA was determined in the presence of various concentrations of the different peptides as described in the experimental procedures. The results obtained were then used to compute the $K_i$ values for the peptides. Each value represents the mean ± S.D. determined from three independent experiments.

Inhibition of Furin, PACE4, PC1 and PC2 by Different L-Polyarginine Peptides. A series of L-polyarginine peptides, with chain lengths of 4 to 9 residues and no terminal modifications, was synthesized and tested for inhibitory potency against furin, PC1, PC2 and PACE4. Table 4 and FIGS. 9(a)-(d) show that the $K_i$ of the L-polyarginine peptides against furin increased from 42 nM to 6 μM as the chain length decreased from 9 to 4 residues. While the $K_i$'s of the nona-, octa-, hepta-, and hexamers ranged from 42 to 114 nM, there was an approximate 10-fold increase in $K_i$ between the hexa- and pentamer, and about a five-fold increase between the penta- and tetramer.

TABLE 4

Inhibition constants of various polyarginine peptides against furin, PACE4 and PC1[d]

| | $K_i$ (μM) | | |
|---|---|---|---|
| | Furin | PACE4 | PC1 |
| Tetra-L-arginine (SEQ ID NO 25) | 6.4 ± 0.9 | >200 | >200 |
| Penta-L-arginine (SEQ ID NO 26) | 0.99 ± 0.08 | 0.98 ± 0.120 | 14 ± 6.1 |
| Hexa-L-arginine (SEQ ID NO 14) | 0.114 ± 0.006 | 0.52 ± 0.045 | 3.9 ± 0.62 |
| Hepta-L-arginine | 0.068 ± 0.001 | 0.24 ± 0.045 | 5.2 ± 1.2 |

TABLE 4-continued

Inhibition constants of various polyarginine peptides against furin, PACE4 and PC1[a]

| | $K_i$ (μM) | | |
|---|---|---|---|
| | Furin | PACE4 | PC1 |
| (SEQ ID NO 27) Octa-L-arginine | 0.061 ± 0.001 | 0.15 ± 0.060 | 5.1 ± 2.0 |
| (SEQ ID NO 28) Nona-L-arginine | 0.042 ± 0.003 | 0.11 ± 0.013 | 12 ± 2.5 |
| (SEQ ID NO 13) Hexa-D-arginine | 0.106 ± 0.010 | 0.58 ± 0.040 | 13 ± 0.25 |

[a]The rate of hydrolysis of pERTKR-MCA was determined in the presence of various concentrations of the different peptides as described in the experimental procedures. The results obtained were then used to compute the $K_i$ values for the peptides. Each value represents the mean ± S.D. determined from three independent experiments.

The $K_i$'s against PACE4 also increased as the chain length of the inhibitor decreased, but unlike furin, the $K_i$ of the pentameric polyarginine (SEQ ID NO 26) was approximately twice that of the hexamer (SEQ ID NO 14), and no sharp change was seen as the chain length was reduced below the n=6 level. The minimum $K_i$ observed was 110 nM. The tetramer (SEQ ID NO 25), however, was not found to inhibit even at mM concentrations. By contrast, the polyarginine peptides were only moderate inhibitors of PC1, with a minimum $K_i$ of ~4 μM. Interestingly, the $K_i$ of the nonamer (SEQ ID NO 13) was significantly greater than those of the hexa-, hepta-, and octamer (SEQ ID NOs 14, 27, and 28, respectively). Similarly to PACE 4 (but not to furin), PC1 was not inhibited by tetra-L-arginine (SEQ ID NO 25) at μM concentrations. Overall, it appeared that the binding pockets of furin and PACE4 were more similar to each other than either was to that of PC1, but that furin has a unique dependence on the S6 binding pocket. (The "S6 binding pocket," in standard nomenclature, is that part of the enzyme that binds the sixth residue of the substrate, counting backward from the scissile bond.)

By contrast to the other proprotein convertases studied here, PC2 activity was consistently stimulated by the polyarginine peptides. The stimulatory effect was noticeable with all polyarginines tested, starting at concentrations as low as 0.1 nM and increasing with concentration up to approximately 10 μM of peptide, following which a relative decrease in activity was observed (data not shown). No effect could be confidently correlated with the peptide length for PC2, except at low nM peptide inhibitor concentrations, where the tetra- and penta-L-arginines (SEQ ID NOs 25 and 26) appeared to produce a smaller stimulatory effect did than the longer peptides (data not shown).

In addition, hexa-D-arginine was synthesized and tested for inhibitory potency against furin, PACE4, PC1, and PC2. The $K_i$'s against furin and PACE4, as shown in Table 4, were remarkably similar to those for hexa-L-arginine, while against PC1 a three-fold increase in $K_i$ was observed. When tested against PC2, no stimulatory or inhibitory effect was observed (results not shown).

Mechanism of Inhibition. Lineweaver-Burk plots for hexa-L-arginine (SEQ ID NO 14), nona-L-arginine (SEQ ID NO 13), and hexa-D-arginine (not shown) demonstrated that, like the acetylated and amidated hexapeptides shown in FIG. 4, these compounds demonstrated strictly competitive-type inhibition. The concentrations of polyarginine used to generate these data were forty-fold lower than the concentrations of amidated and acetylated hexapeptides used in FIG. 4.

Cleavage of Nona-L-arginine (SEQ ID NO 13) and Hexa-L-arginine (SEQ ID NO 14) by Furin. FIGS. 10(*a*) through (*h*) depict the cleavage of nona-L-arginine (SEQ ID NO 13) and hexa-L-arginine (SEQ ID NO 14) by furin. Furin (FIGS. 10(*b*), (*c*), (*d*), (*e*), and (*g*)) or buffer (FIGS. 10(*f*) and (*h*)) was incubated with nona-L-arginine (SEQ ID NO 13) (FIGS. 10(*b*), (*c*), (*d*), (*e*), and (*f*) or hexa-L-arginine (SEQ ID NO 14) (FIGS. (10(*g*) and (*h*) at 37° C. for 0 min (FIG. (10(*b*)), 40 min (FIG. 10(*c*)), 6 h (FIG. 10(*d*)), or 24 h (FIGS. 10(*e*), (*f*), (*g*), and (*h*) prior to separation by HPLC as described in the experimental procedures. In FIG. 10(*a*) the simple separation of a standard mixture polyarginines (without enzyme) is shown; the number of residues per poly-L-arginine is indicated by the positions of the arrows at the tops of FIGS. 10(*a*) and (*e*).

Cleavage of nona-L-arginine (SEQ ID NO 13) was first observed ~40 min after reaction with furin had commenced, with the appearance of hexa- and hepta-L-arginine (FIG. 10(*c*)) (SEQ ID NOs 14 and 27). After four hours penta-L-arginine (SEQ ID NO 26) was also observed, and essentially none of the original nona-L-arginine (SEQ ID NO 13) remained. The heptapeptide (SEQ ID NO 27) was still present after six hours of digestion (FIG. 10(*d*)), but after 24 hours, essentially only the penta- and hexapeptides (SEQ ID NOs 26 and 14) were present (FIG. 10(*e*)). No significant amount of tetra-L-arginine (SEQ ID NO 25) was observed at any time. Cleavage of hexa-L-arginine (SEQ ID NO 14) proceeded much less rapidly than did that of nona-L-arginine (SEQ ID NO 13); indeed essentially no cleavage was seen after six hours incubation with furin (results not shown). After 24 hours, partial digestion of hexa-L-arginine (SEQ ID NO 14) had occurred, producing some penta-L-arginine (SEQ ID NO 26) (FIG. 10(*g*)). Again, essentially no tetra-L-arginine (SEQ ID NO 25) product was seen. Controls, where buffer replaced furin, are shown in FIGS. 10(*f*) and 10(*h*), each after a 24 h incubation at 37° C.

These data show that L-polyarginine is preferentially oriented into the catalytic pocket of furin such that side chains interact with the S1-S6 binding pockets. When the experiment was repeated with hexa-D-arginine and furin, or with nona-L-arginine (SEQ ID NO 13) and PC2, essentially no cleavage was observed after 24 h of incubation (results not shown).

Discussion

We have purified and partially characterized a recombinant, truncated mouse furin from the conditioned medium of CHO cells. Our purified furin preparation was homogeneous, with an apparent molecular weight of 61 kDa by SDS-PAGE and 59 kDa by gel permeation chromatography. The enzyme was shown to be C-terminally processed, as the C-terminally-located tags could not be detected by Western blotting, giving a molecular weight of approximately 60 kDa. Treatment with N-glycosidase F suggested that this furin was glycosylated at two of three potential sites. A truncated furin preparation had previously been shown to be C-terminally processed, with a similar 5 kDa shift in apparent mobility on SDS-PAGE following N-glycosidase F; however, to the best of our knowledge, this is the first time the number of glycosylation sites has been demonstrated. The specific activity of the purified enzyme against pERTKR-MCA of 21 μmol AMC/h was similar to that in a previous report of a maximum specific activity of 30 μmol AMC/h using Boc-RVRR-MCA. The overall yield of 27% was relatively low, probably reflecting the use of two ion-exchange steps in our protocol.

The enzyme suffered only a slight loss of activity at pH 9.0. The pH dependence of furin may depend on the source, substrate, and degree of purification. The purified enzyme used in this study was strongly inhibited by the furin-specific serpin α1-antitrypsin-PDX at concentrations identical with those previously reported.

Basic Residues in all Positions Favor Inhibition of Furin, but not of PC1 and PC2

By contrast to results our laboratory had previously obtained for L-hexapeptide combinatorial library screens against PC1 and PC2, furin revealed a preference for Arg and Lys in all six positions, with Arg being the more inhibitory of the two residues in all positions except P4. In addition, some preference was also shown for His in positions P1, P4, P5 and P6. In contrast, our previous work with PC1 had shown a strong preference for Arg in P1 and P4, Lys in P2, and Leu in P6, while the P3 and P5 residues could be interchanged with relatively little effect on inhibition. Screens against PC2 showed that Arg in positions P1 and P4 consistently gave the highest inhibition, while at the other four positions no clear consensus was seen. Thus it appears that the binding pocket of furin, unlike that of PC1 and PC2, has a preference for basic residues that stretches from the S1 to the S6 subsites. M. Zhong et al., *J. Biol. Chem.*, vol. 274, pp. 33913-33920 (1999) showed that peptides based on the prodomain sequences of both furin and PC7 could act as potent inhibitors of either enzyme: The furin propeptide could be reduced to a ten-residue sequence (QQVAKRRTKR) (SEQ ID NO 29), with a $K_i$ of 40 nM against furin and approximately 500 nM against PC7. When the C-terminal residue was changed to a non-basic alanine, inhibitory potency was abolished. A decapeptide fragment (EQRLLKRAKR) (SEQ ID NO 30) of the propeptide of PC7 showed a $K_i$ of 80 nM towards furin and 6 nM against PC7. It should be noted, however, that differences in the furin preparation and in the methods used to calculate the $K_i$'s preclude direct comparison of our numerical values with those of Zhong et al. Nonetheless, our results show that the inhibitory potency of peptides against furin is correlated with the concentration of positive charges, and indicate that this may be a selective property of furin.

D-Residues can be used to Construct Relatively Potent Inhibitory Peptides

Although the D-hexapeptide screen showed somewhat lower inhibition of furin than did the L-hexapeptide library, the $K_i$'s of the synthetic D-peptides were surprisingly similar to those of the L-peptides (Table 2), indicating a similar mechanism of inhibition. As D-peptides should be more resistant to hydrolysis than L-peptides in vivo, the D-peptides may have greater stability for use as a therapeutic furin inhibitor. D-peptides are completely resistant to hydrolysis by furin.

Furin and PC2 are Sensitive to Groups Distal to the P1 and P6 Residues

We have shown above that furin is sensitive to groups located towards the C-terminal from the P1 side-chain, with a doubling of the $K_i$ upon C-terminal amidation of hexapeptides. We have also shown that furin is sensitive to groups distal to the P6 side chain; N-terminal acetylation of an L-hexapeptide increased its $K_i$ by a factor of eight. These results are consistent with the data of D. Krysan et al., *J. Biol. Chem.*, vol. 274, pp. 23229-23234 (1999), who showed substrate inhibition with hexa- but not tetrapeptide substrates. In the same study a comparison of furin with the related proprotein convertase Kex2 revealed that while the residue at the P1 position had a large effect on catalysis, the P4 and P6 residues were especially important for furin. Furthermore, favorable residues at P2 and P6 were able to compensate for less than optimal residues at P1 and P4. Our data indicated that the effect of acetylation and amidation on the inhibition of PC2 was the opposite of that for furin. However, like furin, P6 acetylation of PC2 inhibitors had the largest single effect on inhibition, demonstrating that, like furin, the binding pocket of PC2 extends beyond the P6 residue.

Hexa-L-arginine (SEQ ID NO 14) is a Potent Inhibitor of Furin, but Stimulates PC2 Activity.

In U. Shinde et al., *Semin. Cell Dev. Biol.*, vol. 11, pp. 35-44 (2000); and A. Basak et al., *Int. J. Pept. Protein Res.*, vol. 44, pp. 253-261 (1994), peptides corresponding to known substrate cleavage sites were used as starting points for the synthesis of peptide inhibitors of furin. A series of deca- and dodecapeptides based upon a partial sequence of the junction between the propeptide domain and the catalytic domain of PC1 were tested for inhibition of PC1 and furin. These peptides contained a variety of unnatural amino acids in the P'1 position. Interestingly, the compounds were found to be slightly better inhibitors of furin than of PC1, with $K_i$'s for the dodecapeptides ranging from 0.8 to 10 µM for furin, compared to 1.0 to 170 µM for PC1. The $K_i$'s of the decapeptides ranged from 1.0 to 8.6 µM against PC1, and from 0.8 to 2.2 µM against furin. While the $K_i$ of the ten-residue propeptide fragment identified by Zhong et al. (1999) was essentially the same as the $K_i$ of nona-L-arginine (SEQ ID NO 13), if cleavage at the P3-P2 bond were to occur, as with nona-L-arginine, the resulting fragment, QQVAKRRT (SEQ ID NO 31), would be expected to have little inhibitory ability due to the lack of a basic residue at P1. In contrast, we observed that cleavage of nona-L-arginine (SEQ ID NO 13) results in peptides having $K_i$'s in the low nanomolar range.

A comparison of inhibition of the proprotein convertases PC1, PC2, furin and PACE4 with polyarginine derivatives revealed striking differences. Whereas furin and PACE4 were both inhibited to approximately the same extent by all polyarginines tested except tetra-L-arginine (SEQ ID NO 25), PC1 was much less sensitive to the peptides than was furin, while PC2 was consistently stimulated. These results suggest that the binding pocket of PACE4 is relatively similar to that of furin.

It has been previously observed that PC2 is fundamentally different from the other members of the proprotein convertase family, for example being the only member requiring the presence of the neuroendocrine protein 7B2 for full activity; activating late in the secretory pathway; and possessing an Asp rather than an Asn in the oxyanion hole. The stimulation of PC2 by L-polyarginines that we observed was not due to more rapid activation of the recombinant proPC2, as maximum activity was attained within 30 min of a reduction in pH from 7.4 to 5.0, irrespective of the presence of polyarginine, and the activity then remained constant for 90 min thereafter (results not shown). Thus it appeared that either a greater proportion of the enzyme preparation was activated by interactions at an allosteric site, or the polyarginine peptides somehow directly assist substrate turnover.

The Furin Catalytic Pocket: Differences with PC1 and PC2

As the polyarginines tested contained the furin cleavage consensus sequence, we expected cleavage to occur in at least some of the polyarginines, an expectation that was confirmed by experimental observations. However, while nona-L-arginine (SEQ ID NO 13) was indeed cleaved by furin, the two primary products were the hexamer (SEQ ID NO 14) and the heptamer (SEQ ID NO 27); the penta-L-arginine (SEQ ID NO 26) product observed after 4 hours (FIG. 10(*e*)) was most likely due to further cleavage of the heptamer (SEQ ID NO 27), as incubation of the hexamer (SEQ ID NO. 14) with furin only produced the pentamer (SEQ ID NO 26) after 24 hours. These results demonstrated that furin does not cleave hexa-L-arginine (SEQ ID NO 14) at the P2 position at a significant rate, an important finding for inhibitors to be used in vivo, in vitro, or ex vivo. It is also interesting that furin showed an absolute preference for substrates having five or six residues N-terminal to the cleavage site over substrates having only two, three, or four residues N-terminal to the cleavage site. This implies that the S6 binding pocket of furin is as important to specificity as are the sites closer to the catalytic triad.

Taken together, our results imply that the furin subsites all appear to be negatively charged, as opposed to those of PC1 and PC2, whose S3 and S6 subsites apparently use hydrophobic interactions, steric interactions, or both. The similar specificity of the polyarginines against PACE4 and furin agrees with observations that these two proprotein convertases are more closely related to each other, both structurally and spatially, than to either PC1 or PC2.

Polyarginines as Therapeutically Useful Furin Inhibitors

Polyarginines, both L- and D-forms, are potent and relatively specific furin inhibitors. We do not expect therapeutic uses of these peptides to be substantially affected by the ability of such highly charged molecules to cross the cell membrane unaided, because one of the defining features of furin is its ability to cycle between the TGN, the cell surface, and the endosomes. For example, it has been shown that α1-PDX can be internalized by cells producing furin, but not by furin-deficient cells. We expect that the internalization of polyarginines by cell-surface exposed furin to be efficient, given their small size and solubility compared to α1-PDX.

Compared to other low molecular weight proprotein convertase inhibitors that have been reported, our preliminary data show that polyarginines have low toxicity at the concentrations needed to inhibit furin. In particular, our results show that the D-polyarginine hexapeptide (D6R) was not toxic to cells, and that it is able to protect cells from killing by diphtheria exotoxin A. These preliminary data are discussed briefly below, and are summarized in Tables 5 and 6.

HEK293 cells were seeded into 96-well plates at the densities indicated. Their growth rates were monitored using the dye WST, which is cleaved by mitochondrial dehydrogenases to a blue dye only in viable cells. The mean absorbance of three wells per condition at 450 nm, plus or minus the standard deviation, is given in Table 5. Table 5 shows that the addition of D-hexa-arginine (D6R) at the concentrations shown did not significantly affect the growth of the cells. We concluded that D6R did not appear to be cytotoxic even at 100 μM (final concentration).

Therapeutic Applications

The administration of polyarginines and other polybasic peptides in accordance with the present invention may be used to combat bacterial and viral infections, and to inhibit the growth of certain cancers. Preliminary data, for example, show activity against *Pseudomonas* exotoxin, and against HIV. For example, preliminary data (not shown) suggested that micromolar concentrations of D-hexa-arginine inhibited the formation of syncytia by HIV in vitro in the MT4 line of T cells.

Furin is thought to play a role in the pathogenesis of many viruses and bacteria. See S. Molloy et al., "Bi-cycling the furin pathway: from TGN localization to pathogen activation and embryogenesis," *Trends in Cell Biology*, vol. 9, pp. 28-35 (1999). Examples include bacteria that produce toxins that require furin-mediated cleavage for entry into the cell, such as *Pseudomonas* exotoxin A, diphtheria toxin, and anthrax protective antigen. Certain human and animal viruses contain glycoproteins that must be cleaved by host cell furin before infectious particles can formed. Examples of such viruses include HIV and other retroviruses, fowl plague influenza virus, Semliki forest virus, Newcastle disease virus, parainfluenza virus, measles, herpes, and Ebola. Furin thus represents a target for therapeutic attack. Although furin is required for the production of many important cellular proteins, healthy cell lines exist that do not contain furin; suggesting that furin is not absolutely required for mammalian cell

TABLE 5

| Time (hour) | Life curve $5 \times 10^2$ cells/well | 2 μM D6R | 4 μM D6R | 6 μM D6R | 8 μM D6R | 10 μM D6R | 30 μM D6R | 60 μM D6R | 100 μM D6R |
|---|---|---|---|---|---|---|---|---|---|
| 2.5 | 0.05 ± 0.01 | | | | | | | | |
| 24 | 0.27 ± 0.04 | | | | | | | | |
| 48 | 0.63 ± 0.02 | | | | | | | | |
| 51 | 0.65 ± 0.03 | 0.69 ± 0.02 | 0.64 ± 0.03 | 0.63 ± 0.04 | 0.67 ± 0.01 | 0.64 ± 0.03 | 0.64 ± 0.02 | 0.66 ± 0.05 | 0.62 ± 0.03 |
| 75 | 1.25 ± 0.02 | 1.25 ± 0.11 | 1.28 ± 0.14 | 1.13 ± 0.14 | 1.36 ± 0.08 | 1.28 ± 0.14 | 1.29 ± 0.08 | 1.17 ± 0.08 | 1.19 ± 0.11 |
| 99 | 1.46 ± 0.05 | 1.42 ± 0.02 | 1.39 ± 0.06 | 1.48 ± 0.04 | 1.40 ± 0.05 | 1.49 ± 0.08 | 1.45 ± 0.06 | 1.48 ± 0.06 | 1.47 ± 0.09 |

*Pseudomonas* exotoxin A (PEA) must be cleaved by furin at the cell surface to gain entry into a cell, which typically causes cell death. Table 6 shows that the addition of PEA to logarithmically growing HEK293 cells at a concentration of 10 ng/mL caused death of many cells, evidenced by a decrease in the amount of WST at all times, as compared to wells lacking PEA. However, adding D-hexa-arginine at 1 μM final concentration reduced the cell death caused by PEA. We inferred that the D6R blocked the cleavage of PEA by furin, thus preventing its activation.

growth. It is likely that the temporary use of drugs affecting furin can promote the antibacterial or antiviral activities of concurrently used drugs acting by different mechanisms, thus selectively affecting pathogenesis rather than normal cellular activities.

Furin is also thought to be involved in the degradation of extracellular matrix through its ability to activate precursors of matrix metalloproteinases (MMPs), in particular MMP-1. Since MMP expression increases in many tumor cell types and has been implicated in metastatic progression, inhibition

TABLE 6

| Time (hours) | Life curve $5 \times 10^2$ cells/well | 0 D6R 0 PEA | 0 D6R 10 ng/mL PEA | 1 μM D6R 10 ng/mL PEA | 10 μM D6R 10 ng/mL PEA | 100 μM D6R 10 ng/mL PEA |
|---|---|---|---|---|---|---|
| 2.5 | 0.09 ± 0.01 | | | | | |
| 24 | 0.26 ± 0.03 | | | | | |
| 48 | 0.45 ± 0.02 | | | | | |
| 51 | 0.53 ± 0.02 | 0.58 ± 0.02 | 0.46 ± 0.03 | 0.52 ± 0.04 | 0.54 ± 0.07 | 0.51 ± 0.04 |
| 76 | 1.00 ± 0.06 | 1.03 ± 0.09 | 0.63 ± 0.01 | 0.85 ± 0.02 | 0.73 ± 0.05 | 0.78 ± 0.03 |
| 86 | 1.15 ± 0.01 | 1.17 ± 0.04 | 0.38 ± 0.04 | 0.83 ± 0.02 | 0.71 ± 0.02 | 0.61 ± 0.06 |
| 96 | 1.65 ± 0.05 | 1.65 ± 0.03 | 0.21 ± 0.02 | 0.56 ± 0.04 | 0.67 ± 0.01 | 0.55 ± 0.02 | of MMP activation by inhibiting furin may result in the slowing of tumor progression. Thus furin may represent a logical candidate for an anti-cancer drug.

Peptides that may be used in the present invention may have from about 4 to about 20 amino acids, preferably from about 6 to about 10 amino acids. Not only are polyarginines useful in the present invention, but so are peptides comprising other basic amino acid residues, both naturally occurring, such as lysine and histidine, but also non-natural or unusual basic amino acids, such as homoarginine, ornithine, diaminobutyric acid, and diaminopropionic acid. The amino acids may be D-form or L-form. Without wishing to be bound by this theory, it is believed that peptides having at least 4, preferably 6 to 9, consecutive basic amino acid residues will have the greatest anti-furin activity.

As discussed above, it can be helpful to remove the acetyl and amide groups on the ends of the peptide to increase inhibitory effects, particularly the acetyl group.

As discussed above, peptides comprising D-amino acids are also useful in practicing this invention. Their inhibitory effects are comparable to, though somewhat lower than those of the otherwise-identical peptides consisting of L-amino acids. However, since their biological half-lives will in general be longer, D-amino acid peptides may have advantages over L-amino acid peptides in practicing this invention in vivo. D-nona-arginine, for example, is expected to be a useful anti-furin compound.

This method of treatment may be used in vertebrates generally, including human and non-human mammals, birds, fish, reptiles, and amphibians. Peptides in accordance with the present invention may be administered to a patient by any suitable means, including oral, intravenous, parenteral, subcutaneous, intrapulmonary, and intranasal administration. Oral administration may be best suited for D-form peptides, since they are not broken down digestively. Oral administration of D-form peptides may be enhanced by linking the peptide to a suitable carrier to facilitate uptake by the intestine, for example vitamin $B_{12}$, following generally the $B_{12}$-conjugation technique of G. Russell-Jones et al., "Synthesis of LHRH Antagonists Suitable for Oral Administration via the Vitamin $B_{12}$ Uptake System," *Bioconjugate Chem.*, vol. 6, pp. 34-42 (1995).

Parenteral infusions include intramuscular, intravenous, intraarterial, or intraperitoneal administration. The compound may also be administered transdermally, for example in the form of a slow-release subcutaneous implant, or orally in the form of capsules, powders, or granules. It may also be administered by inhalation.

Pharmaceutically acceptable carrier preparations for parenteral administration include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

The form may vary depending upon the route of administration. For example, compositions for injection may be provided in the form of an ampule, each containing a unit dose amount, or in the form of a container containing multiple doses.

The compound may be formulated into therapeutic compositions as pharmaceutically acceptable salts. These salts include acid addition salts formed with inorganic acids, for example hydrochloric or phosphoric acid, or organic acids such as acetic, oxalic, or tartaric acid, and the like. Salts also include those formed from inorganic bases such as, for example, sodium, potassium, ammonium, calcium or ferric hydroxides, and organic bases such as isopropylamine, trimethylamine, histidine, procaine and the like. The compositions may be administered intravenously, subcutaneously, intramuscularly, or (especially when in D-amino acid form and complexed with a carrier such as vitamin $B_{12}$) orally.

Controlled delivery may be achieved by admixing the active ingredient with appropriate macromolecules, for example, polyesters, polyamino acids, polyvinyl pyrrolidone, ethylenevinylacetate, methylcellulose, carboxymethylcellulose, prolamine sulfate, or lactide/glycolide copolymers. The rate of release of the active compound may be controlled by altering the concentration of the macromolecule.

Another method for controlling the duration of action comprises incorporating the active compound into particles of a polymeric substance such as a polyester, peptide, hydrogel, polylactide/glycolide copolymer, or ethylenevinylacetate copolymers. Alternatively, an active compound may be encapsulated in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

An "effective amount" of a peptide is an amount that inhibits the activity of furin by a statistically significant degree; or that inhibits the growth, metabolism, or reproduction of bacteria or viruses to a statistically significant degree; or that inhibits the growth or metastasis of a tumor to a statistically significant degree; or that ablates the tumor to a statistically significant degree. "Statistical significance" is determined as the $P<0.05$ level, or by such other measure of statistical significance as is commonly used in the art for a particular type of experimental determination.

The complete disclosures of all references cited in this specification are hereby incorporated by reference. Also incorporated by reference is the full disclosure of the following paper, which is not prior art to this application: A. Cameron et al., "Polyarginines are potent furin inhibitors," *J. Biol. Chem.* vol. 275, pp. 36741-36749 (2000). In the event of an otherwise irreconcilable conflict, however, the present specification shall control.

Abbreviations

Some of the abbreviations used in the specification follow:
Abz: o-aminobenzoyl
eddnp: ethylenediamine 2,4-dinitrophenyl
α1-PDX: α1-antitrypsin Portland
AMC: aminomethylcoumarin
D6R: D-polyarginine hexapeptide
TFA: trifluoroacetic acid
MCA: methylcoumarinamide
HEPES: N-[2-hydroxethyl]piperazine-N'-[2-ethanesulfonic acid]
MMPs: matrix metalloproteinases
MBP: major basic protein.

We claim:

1. A method for inhibiting the growth or metastasis of a tumor in a mammalian host, wherein the growth or metastasis of the tumor depends upon furin; said method comprising administering to a human host a polyarginine, wherein the polyarginine is from four to twenty arginine residues; wherein the host has a tumor; wherein the growth or metastasis of the tumor depends upon furin; and wherein the amount of the polyarginine administered to the host is an effective amount for inhibiting the growth or metastasis of the tumor.

2. The method of claim 1, wherein the polyarginine is from six to ten arginine residues.

3. The method of claim 1, wherein the polyarginine comprises L-form arginine residues.

4. The method of claim 1, wherein the polyarginine comprises D-form arginine residues.

5. The method of claim 1, wherein the polyarginine is tetra-L-arginine (SEQ ID NO 25), penta-L-arginine (SEQ ID NO 26), hexa-L-arginine (SEQ ID NO 14), hepta-L-arginine (SEQ ID NO 27), octa-L-arginine (SEQ ID NO 28), or nona-L-arginine (SEQ ID NO 13).

6. The method of claim 1, wherein the polyarginine is tetra-D-arginine, penta-D-arginine, hexa-D-arginine, hepta-D-arginine, octa-D-arginine, or nona-D-arginine.

7. The method of claim 1, wherein the polyarginine lacks an N-terminal acetyl group, or wherein the polyarginine lacks a C-terminal amide group, or wherein the polyarginine lacks both an N-terminal acetyl group and a C-terminal amide group.

8. The method of claim 1, wherein the polyarginine is hexa-L-arginine (SEQ ID NO: 14) or hexa-D-arginine.

9. The method of claim 1, wherein metastasis of the tumor depends upon furin-assisted maturation of the matrix-metalloproteinase MT1-MMP or of the matrix-metalloproteinase stromelysin-3; wherein the polyarginine inhibits the activity of furin; and wherein the polyarginine-inhibited decline in furin activity inhibits metastasis of the tumor.

* * * * *

UNITED STATES PATENT AND TRADEMARK OFFICE
CERTIFICATE OF CORRECTION

PATENT NO. : 7,569,547 B2
APPLICATION NO. : 11/408519
DATED : August 4, 2009
INVENTOR(S) : Lindberg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 278 days.

Signed and Sealed this

Seventh Day of September, 2010

David J. Kappos
*Director of the United States Patent and Trademark Office*

SEQUENCE LISTING

<160> NUMBER OF SEQ ID NOS: 31

<210> SEQ ID NO 1
<211> LENGTH: 4
<212> TYPE: PRT
<213> ORGANISM: Artificial Sequence
<220> FEATURE:
<221> NAME/KEY: misc_feature
<222> LOCATION: 2..3
<223> OTHER INFORMATION: Xaa in position two denotes any amino acid.
      Xaa in position three denotes Lys or Arg.
      This is the reported consensus sequence for
      furin cleavage.

<400> SEQUENCE: 1

Arg Xaa Xaa Arg
1

<210> SEQ ID NO 2
<211> LENGTH: 4
<212> TYPE: PRT
<213> ORGANISM: Artificial Sequence
<220> FEATURE:
<221> NAME/KEY: misc_feature
<222> LOCATION: 2..3
<223> OTHER INFORMATION: Xaa in position two denotes any amino acid.
      Xaa in position three denotes any amino acid.
      This is the reported minimum consensus sequence for
      furin cleavage.

<400> SEQUENCE: 2

Arg Xaa Xaa Arg
1

<210> SEQ ID NO 3
<211> LENGTH: 7
<212> TYPE: PRT
<213> ORGANISM: Meleagris gallopavo

<400> SEQUENCE: 3

Lys Pro Ala Cys Thr Leu Glu
1               5

<210> SEQ ID NO 4
<211> LENGTH: 7
<212> TYPE: PRT
<213> ORGANISM: Artificial Sequence
<220> FEATURE:
<221> NAME/KEY: misc_feature
<223> OTHER INFORMATION: Designed peptide.  This is an engineered
      modification of SEQ ID NO: 3, which is in
      turn derived from Meleagris gallopavo.

<400> SEQUENCE: 4

Lys Pro Arg Cys Lys Arg Glu
1               5

<210> SEQ ID NO 5
<211> LENGTH: 7
<212> TYPE: PRT
<213> ORGANISM: Homo sapiens

<400> SEQUENCE: 5

Leu Glu Ala Ile Met Pro Ser
1               5

```
<210> SEQ ID NO 6
<211> LENGTH: 7
<212> TYPE: PRT
<213> ORGANISM: Artificial Sequence
<220> FEATURE:
<221> NAME/KEY: misc_feature
<223> OTHER INFORMATION: Designed peptide.  This is an engineered
      modification of SEQ ID NO: 5, which is in
      turn derived from Homo sapiens.

<400> SEQUENCE: 6

Leu Glu Arg Ile Met Arg Ser
1               5

<210> SEQ ID NO 7
<211> LENGTH: 10
<212> TYPE: PRT
<213> ORGANISM: Artificial Sequence
<220> FEATURE:
<221> NAME/KEY: misc_feature
<223> OTHER INFORMATION: Region of the protease inhibitor alpha-2-
      macroglobulin.

<400> SEQUENCE: 7

Arg Val Gly Phe Tyr Glu Ser Asp Val Met
1               5                   10

<210> SEQ ID NO 8
<211> LENGTH: 10
<212> TYPE: PRT
<213> ORGANISM: Artificial Sequence
<220> FEATURE:
<221> NAME/KEY: misc_feature
<223> OTHER INFORMATION: Designed peptide.  This is an engineered
      modification of SEQ ID NO: 7, which is in
      turn a region of alpha-2-macroglobulin.

<400> SEQUENCE: 8

Arg Val Gly Phe Tyr Glu Ser Asp Val Met
1               5                   10

<210> SEQ ID NO 9
<211> LENGTH: 10
<212> TYPE: PRT
<213> ORGANISM: Homo sapiens

<400> SEQUENCE: 9

Val Val Arg Asn Ser Arg Cys Ser Arg Met
1               5                   10

<210> SEQ ID NO 10
<211> LENGTH:
<212> TYPE:
<213> ORGANISM:

<400> SEQUENCE: 10

000

<210> SEQ ID NO 11
<211> LENGTH:
<212> TYPE:
<213> ORGANISM:

<400> SEQUENCE: 11

000

<210> SEQ ID NO 12
```

```
<211> LENGTH:
<212> TYPE:
<213> ORGANISM:

<400> SEQUENCE: 12

000

<210> SEQ ID NO 13
<211> LENGTH: 9
<212> TYPE: PRT
<213> ORGANISM: Artificial Sequence
<220> FEATURE:
<221> NAME/KEY: misc_feature
<223> OTHER INFORMATION: De novo designed peptide

<400> SEQUENCE: 13

Arg Arg Arg Arg Arg Arg Arg Arg Arg
1               5

<210> SEQ ID NO 14
<211> LENGTH: 6
<212> TYPE: PRT
<213> ORGANISM: Artificial Sequence
<220> FEATURE:
<221> NAME/KEY: misc_feature
<223> OTHER INFORMATION: De novo designed peptide

<400> SEQUENCE: 14

Arg Arg Arg Arg Arg Arg
1               5

<210> SEQ ID NO 15
<211> LENGTH: 6
<212> TYPE: PRT
<213> ORGANISM: Artificial Sequence
<220> FEATURE:
<221> NAME/KEY: misc_feature
<223> OTHER INFORMATION: De novo designed peptide

<400> SEQUENCE: 15

His His His His His His
1               5

<210> SEQ ID NO 16
<211> LENGTH: 6
<212> TYPE: PRT
<213> ORGANISM: Artificial Sequence
<220> FEATURE:
<221> NAME/KEY: misc_feature
<223> OTHER INFORMATION: De novo designed peptide

<400> SEQUENCE: 16

His His Lys Arg Arg Arg
1               5

<210> SEQ ID NO 17
<211> LENGTH: 6
<212> TYPE: PRT
<213> ORGANISM: Artificial Sequence
<220> FEATURE:
<221> NAME/KEY: misc_feature
<223> OTHER INFORMATION: De novo designed peptide

<400> SEQUENCE: 17

Met His Lys Arg Arg Arg
1               5
```

```
<210> SEQ ID NO 18
<211> LENGTH: 6
<212> TYPE: PRT
<213> ORGANISM: Artificial Sequence
<220> FEATURE:
<221> NAME/KEY: misc_feature
<223> OTHER INFORMATION: De novo designed peptide

<400> SEQUENCE: 18

Lys His Lys Arg Arg Arg
1               5

<210> SEQ ID NO 19
<211> LENGTH: 6
<212> TYPE: PRT
<213> ORGANISM: Artificial Sequence
<220> FEATURE:
<221> NAME/KEY: misc_feature
<223> OTHER INFORMATION: De novo designed peptide

<400> SEQUENCE: 19

Arg His Lys Arg Arg Arg
1               5

<210> SEQ ID NO 20
<211> LENGTH: 6
<212> TYPE: PRT
<213> ORGANISM: Artificial Sequence
<220> FEATURE:
<221> NAME/KEY: misc_feature
<223> OTHER INFORMATION: De novo designed peptide

<400> SEQUENCE: 20

His Arg Lys Arg Arg Arg
1               5

<210> SEQ ID NO 21
<211> LENGTH: 5
<212> TYPE: PRT
<213> ORGANISM: Artificial Sequence
<220> FEATURE:
<221> NAME/KEY: misc_feature
<223> OTHER INFORMATION: De novo designed peptide

<400> SEQUENCE: 21

Met Arg Lys Arg Arg
1               5

<210> SEQ ID NO 22
<211> LENGTH: 6
<212> TYPE: PRT
<213> ORGANISM: Artificial Sequence
<220> FEATURE:
<221> NAME/KEY: misc_feature
<223> OTHER INFORMATION: De novo designed peptide

<400> SEQUENCE: 22

Lys Arg Lys Arg Arg Arg
1               5

<210> SEQ ID NO 23
<211> LENGTH: 6
<212> TYPE: PRT
<213> ORGANISM: Artificial Sequence
<220> FEATURE:
<221> NAME/KEY: misc_feature
<223> OTHER INFORMATION: De novo designed peptide

<400> SEQUENCE: 23
```

Arg Arg Lys Arg Arg Arg
1               5

<210> SEQ ID NO 24
<211> LENGTH: 6
<212> TYPE: PRT
<213> ORGANISM: Artificial Sequence
<220> FEATURE:
<221> NAME/KEY: misc_feature
<223> OTHER INFORMATION: De novo designed peptide

<400> SEQUENCE: 24

Leu Leu Arg Val Lys Arg
1               5

<210> SEQ ID NO 25
<211> LENGTH: 4
<212> TYPE: PRT
<213> ORGANISM: Artificial Sequence
<220> FEATURE:
<221> NAME/KEY: misc_feature
<223> OTHER INFORMATION: De novo designed peptide

<400> SEQUENCE: 25

Arg Arg Arg Arg
1

<210> SEQ ID NO 26
<211> LENGTH: 5
<212> TYPE: PRT
<213> ORGANISM: Artificial Sequence
<220> FEATURE:
<221> NAME/KEY: misc_feature
<223> OTHER INFORMATION: De novo designed peptide

<400> SEQUENCE: 26

Arg Arg Arg Arg Arg
1               5

<210> SEQ ID NO 27
<211> LENGTH: 7
<212> TYPE: PRT
<213> ORGANISM: Artificial Sequence
<220> FEATURE:
<221> NAME/KEY: misc_feature
<223> OTHER INFORMATION: De novo designed peptide

<400> SEQUENCE: 27

Arg Arg Arg Arg Arg Arg Arg
1               5

<210> SEQ ID NO 28
<211> LENGTH: 8
<212> TYPE: PRT
<213> ORGANISM: Artificial Sequence
<220> FEATURE:
<221> NAME/KEY: misc_feature
<223> OTHER INFORMATION: De novo designed peptide

<400> SEQUENCE: 28

Arg Arg Arg Arg Arg Arg Arg Arg
1               5

<210> SEQ ID NO 29
<211> LENGTH: 10
<212> TYPE: PRT
<213> ORGANISM: Artificial Sequence

```
<220> FEATURE:
<221> NAME/KEY: misc_feature
<223> OTHER INFORMATION: Ten-residue sequence from furin propeptide.

<400> SEQUENCE: 29

Gln Gln Val Ala Lys Arg Arg Thr Lys Arg
1               5                   10

<210> SEQ ID NO 30
<211> LENGTH: 10
<212> TYPE: PRT
<213> ORGANISM: Artificial Sequence
<220> FEATURE:
<221> NAME/KEY: misc_feature
<223> OTHER INFORMATION: Decapeptide fragment of the propeptide of PC7

<400> SEQUENCE: 30

Glu Gln Arg Leu Leu Lys Arg Ala Lys Arg
1               5                   10

<210> SEQ ID NO 31
<211> LENGTH: 8
<212> TYPE: PRT
<213> ORGANISM: Artificial Sequence
<220> FEATURE:
<221> NAME/KEY: misc_feature
<223> OTHER INFORMATION: Hypothesized furin cleavage fragment

<400> SEQUENCE: 31

Gln Gln Val Ala Lys Arg Arg Thr
1               5
```